United States Patent
Mahoney et al.

(10) Patent No.: US 11,324,995 B2
(45) Date of Patent: May 10, 2022

(54) REHABILITATION AID

(71) Applicant: E2L Products Limited, Monmouth (GB)

(72) Inventors: Stchevereuil Darcy Boyd Mahoney, Monmouth (GB); David Burnham Haxworth, Monmouth (GB)

(73) Assignee: E2L PRODUCTS LIMITED, Monmouth (GB)

(*) Notice: Subject to any disclaimer, the term of this patent is extended or adjusted under 35 U.S.C. 154(b) by 0 days.

(21) Appl. No.: 16/469,847

(22) PCT Filed: Dec. 11, 2017

(86) PCT No.: PCT/GB2017/000176
§ 371 (c)(1),
(2) Date: Jun. 14, 2019

(87) PCT Pub. No.: WO2018/115803
PCT Pub. Date: Jun. 28, 2018

(65) Prior Publication Data
US 2019/0365591 A1    Dec. 5, 2019

(30) Foreign Application Priority Data

Dec. 21, 2016 (GB) .................................... 1621918

(51) Int. Cl.
*A63B 23/035* (2006.01)
*A63B 22/00* (2006.01)
(Continued)

(52) U.S. Cl.
CPC ........ *A63B 22/20* (2013.01); *A63B 21/00181* (2013.01); *A63B 21/285* (2013.01);
(Continued)

(58) Field of Classification Search
CPC ...... B23Q 9/00; B23Q 9/0007; B23Q 9/0014; B23Q 9/0021; B23Q 9/0028;
(Continued)

(56) References Cited

U.S. PATENT DOCUMENTS 4,463,947 A    8/1984 Kloenne
4,569,336 A    2/1986 Wheeler
(Continued)

FOREIGN PATENT DOCUMENTS

AU    2014202518    5/2014
DE    10053976    5/2002
(Continued)

OTHER PUBLICATIONS

Bob's Plans, Table Saw Sled safety Handles [online], published Mar. 27, 2015, [retrieved on Nov. 5, 2020], <URL: https://web.archive.org/web/20150810013054/https://www.bobsplans.com/TableSawJigs/TenoningJig.htm>(Year: 2015).*
(Continued)

*Primary Examiner* — Nyca T Nguyen
*Assistant Examiner* — Zachary T Moore
(74) *Attorney, Agent, or Firm* — Carter, DeLuca & Farrell LLP; George Likourezos

(57) ABSTRACT

A rehabilitation therapy aid (FIG. 4), for use in aiding a patient to regain and improve movement and control in a limb, comprises a moveable structure (51) having engagement means (53) whereby the structure can be moved by the limb of a patient (72) requiring therapy and separate engagement means (52) whereby the structure can be moved in the same direction by a therapist (71) or by the patient's stronger limb. A movement detector (56) is arranged so that the movement of the structure (51) can be tracked by the patient and/or by the therapist.

19 Claims, 20 Drawing Sheets

(51) Int. Cl.
  *A63B 23/12* (2006.01)
  *A63B 21/28* (2006.01)
  *A61B 5/11* (2006.01)
  *A63B 22/20* (2006.01)
  *A63B 21/00* (2006.01)
  *A61H 1/02* (2006.01)

(52) U.S. Cl.
  CPC .......... *A63B 21/4017* (2015.10); *A63B 22/00* (2013.01); *A63B 23/035* (2013.01); *A63B 23/1209* (2013.01); *A61B 5/1124* (2013.01); *A61H 1/0237* (2013.01); *A61H 1/0274* (2013.01); *A61H 2201/1276* (2013.01); *A61H 2201/1638* (2013.01); *A61H 2201/1642* (2013.01); *A61H 2201/1652* (2013.01); *A61H 2201/5064* (2013.01); *A63B 21/0004* (2013.01); *A63B 21/28* (2013.01); *A63B 2022/0092* (2013.01); *A63B 2022/0094* (2013.01)

(58) Field of Classification Search
  CPC .. B23Q 9/0035; B23Q 9/0064; B23Q 9/0071; B23Q 9/0078; B27C 5/02; B27C 5/04; B27C 5/06; B27C 5/10; G09B 23/30; G09B 23/32; G09B 23/34; A61H 2201/1253; A61H 2201/1261; A61H 2201/1269; A61H 2201/1276; A61H 2201/1635; A61H 2201/1638; A61H 2205/065; A61H 1/0274; A61H 1/0285; A63B 21/28; A63B 21/285; A63B 21/4033; A63B 21/4035; A63B 21/4045; A63B 22/20; A63B 22/201; A63B 22/203; A63B 23/03508; A63B 23/03525; A63B 23/0355; A63B 23/12; A63B 23/1209; A63B 23/16
  See application file for complete search history.

(56) References Cited

U.S. PATENT DOCUMENTS

| | | | | |
|---|---|---|---|---|
| 5,454,774 A * | 10/1995 | Davis | ...................... | A63B 22/18 482/146 |
| 5,466,213 A | 11/1995 | Hogan et al. | | |
| 6,149,612 A * | 11/2000 | Schnapp | ............... | A61H 1/0285 482/44 |
| 6,325,023 B1 | 12/2001 | Elnatan | | |
| 7,311,643 B2 * | 12/2007 | Sheeks | ............. | A63B 21/00192 482/142 |
| 9,026,242 B2 * | 5/2015 | Rivers | .................. | B23Q 9/0042 700/192 |
| 9,265,685 B1 * | 2/2016 | McAmis | ............ | A63B 71/0622 |
| 10,058,729 B2 * | 8/2018 | Choi | ....................... | A63B 23/12 |
| 10,299,979 B2 * | 5/2019 | Sapin | ................. | A63B 21/4045 |
| 10,299,980 B2 * | 5/2019 | Ban | ........................ | A63B 23/14 |
| 2007/0021692 A1 * | 1/2007 | Cornacchiari | .......... | A63B 23/14 601/5 |
| 2008/0248927 A1 * | 10/2008 | Ivey | ...................... | A61H 1/0285 482/44 |
| 2011/0295165 A1 * | 12/2011 | Cavallaro | .............. | A63B 22/20 601/33 |
| 2012/0157274 A1 * | 6/2012 | MacColl | ............ | A63B 23/0211 482/132 |
| 2013/0059696 A1 * | 3/2013 | Hijmans | ................ | A63F 13/213 482/8 |
| 2014/0366386 A1 * | 12/2014 | Brisson | .................. | B23Q 35/00 30/273 |
| 2015/0313793 A1 * | 11/2015 | Lee | ......................... | A61H 99/00 434/257 |
| 2016/0005338 A1 * | 1/2016 | Melendez-Calderon | | ..................... G09B 23/32 434/267 |
| 2017/0340502 A1 * | 11/2017 | Roh | ...................... | A63B 23/035 |
| 2017/0354839 A1 * | 12/2017 | Reque | ................ | A63B 21/4039 |
| 2018/0221698 A1 * | 8/2018 | Heathfield | .............. | A63B 21/22 |

FOREIGN PATENT DOCUMENTS

| | | | | |
|---|---|---|---|---|
| DE | 202004015122 | | 12/2004 | |
| EP | 2156815 | | 2/2010 | |
| EP | 2298266 | | 3/2011 | |
| JP | 2004057565 | | 2/2004 | |
| JP | 2004057565 A | * | 2/2004 | |
| KR | 20140029172 A | * | 3/2014 | ............ B25J 9/0006 |
| KR | 101507700 | | 4/2015 | |
| WO | WO 2005060913 | | 7/2005 | |
| WO | WO 2010059066 | | 5/2010 | |
| WO | WO 2014042323 | | 3/2014 | |

OTHER PUBLICATIONS

Fine Woodworking, Physical therapy in the shop [online], Published Aug. 16, 2015. Retrieved from the Internet <URL: https://www.finewoodworking.com/readerproject/2015/08/16/physical-therapy-in-the-shop> (Year: 2015).*

International Search Report dated Mar. 9, 2018 corresponding to Int'l Patent Application PCT/GB2017/000176; (4 pp).

Corresponding German Examination Report dated Nov. 16, 2021 for Application No. GB1621918.0 ( 8 pages).

* cited by examiner

REHABILITATION AID

This invention relates to a rehabilitation aid for use in aiding a patient to regain and improve movement and control in a limb. It is of particular use during recuperation after a stroke (cerebrovascular insult) and can be of use during recuperation after massive trauma resulting from a head injury or spinal injury or in therapy for children with cerebral palsy.

During a stroke, poor blood flow to the brain results in cell death so that part of the brain does not function properly. Frequently, this results in hemiplegia, that is loss or impairment of movement of the muscles in one limb or on one side of the body. Therapists (physiotherapists and/or occupational therapists) can work with patients to improve awareness and use of the hemiplegic side. One example physiotherapists employ to promote motor learning involves constraint-induced movement therapy. Through continuous practice the patient relearns to use and adapt the hemiplegic limb during functional activities.

Robots have been developed to aid rehabilitation, for example by active assisted exercise, in which the robot helps the patient to move his or her hand or arm in a predetermined pathway. An example of an interactive robotic therapist is described in U.S. Pat. No. 5,466,213. A moveable member driven by a programmed drive system is secured to a patient's arm and can guide the patient through a desired series of exercises, which may be presented as video games. The robot can assist the patient in moving the robot arm if it senses that the patient is struggling.

Other examples of computer-aided devices for rehabilitation training are described in DE-10053976, DE-OLS-202004015122, WO 2014042323 and in KR 101507700. DE-10053976 describes a therapeutic electromechanic exerciser having two mechanical arms which each carry a handle and are controllable to be independently or interdependently movable. Each arm can be controlled either in passive (motorised) mode or in active mode where the patient's arm is active against an adjustable power resistor. DE-OLS-202004015122 describes a training tool to strengthen the hand and arm muscles achieved in that two rails are mounted on a base plate parallel at a distance about shoulder width of a human. A rod connects blocks which slide in the rails. The devices of DE-10053976 and DE-OLS-202004015122 are designed as bilateral upper limb training devices. WO 2010/059066 describes a similar device.

Rehabilitation robots, such as that described in U.S. Pat. No. 5,466,213, have the advantage that a process or exercise can easily be repeated as many times as required. Frequent target-oriented movements are beneficial for regaining arm movement when recuperating from a stroke. It can also quantify the improvement achieved by a patient over a series of exercises. U.S. Pat. No. 5,466,213 suggests further advantages that the interactive robotic therapist allows a therapist to rehabilitate multiple patients at one time and the therapist can provide a patient with therapy by controlling a remotely located robotic therapist. However, the robotic therapist is an expensive machine which is not transportable, so that in practice each robotic therapist is located in a hospital and the patient has to visit the hospital for a rehabilitation session, usually in the presence of the therapist. There is a need for a rehabilitation aid which is less expensive, and preferably transportable, while still aiding frequent target-oriented movements.

A rehabilitation therapy aid according to one aspect of the present invention comprises a moveable structure, free to move in any direction across a surface on or above the surface, the structure having first engagement means whereby the structure can be moved by the limb of a patient requiring therapy and separate second engagement means whereby the structure can be moved in the same direction by a therapist, or by the patient's stronger limb, and a sensor or movement detector arranged so that the movement of the structure can be tracked.

A rehabilitation therapy aid according to another aspect of the invention comprises a moveable structure having first engagement means whereby the structure can be moved by a patient and separate second engagement means whereby the structure can be moved in the same direction by a therapist, the second engagement means being concealed from view, and a movement detector arranged so that the movement of the structure can be tracked.

In a rehabilitation process according to the invention, a patient engages a movable structure to move or attempt to move the structure in a target direction and a therapist engages the moveable structure by concealed means so that the therapist moves the structure in the same target direction.

The rehabilitation therapy aid is generally designed to help exercise one of a patient's limbs. Most frequently the therapy aid is used for rehabilitation of the arm and hand, since many stroke victims regain their ability to walk, but fewer regain enough arm and hand movement and control for everyday tasks such as dressing or eating with a knife and fork. However a therapy aid according to the invention with a different type of movable structure can be designed to help exercise the leg.

The rehabilitation therapy aid of the invention makes it easier for a therapist to help the patient's movements to the necessary degree, thus allowing more repetitions of exercises within each rehabilitation therapy session. The rehabilitation therapy aid of the invention also allows a qualified physiotherapist or occupational therapist to teach an untrained person, for example a relative or friend of the patient, to help in certain targeted movements which the qualified therapist considers most beneficial for that patient. The relative or friend can then, using the therapy aid of the invention, help the patient to carry out many more repetitions of those targeted movements. This is a particular advantage of the simple form of the invention in which the moveable structure is free to move in any direction across a surface.

Many forms of rehabilitation therapy aid according to the invention can also be used by a patient alone, using the patient's stronger limb to aid the movements of the limb requiring therapy. This can be helpful for patients who have regained some movement and control in the affected limb but need further practice to improve control of the direction of movement.

When used to aid a patient who has lost movement of the muscles in one limb as a result of a cerebrovascular insult, the rehabilitation therapy aid of the invention helps to rebuild neurological pathways connecting the brain and the limb. The therapy aid and rehabilitation process are designed so that the patient perceives that the damaged limb is at least partly effective in moving the structure in the target direction even when the structure is being moved by the therapist. Repetition of this helps to rebuild neurological pathways, so that the damaged limb does become effective in moving the structure in the target direction.

The patient's perception is affected by having the patient's arm in sight whilst completing exercises that engage the brain while the arm providing assistance is hidden. When operating the device of DE-10053976, the patient is aware that his brain is telling the strong arm to do the work. Therapy aids according to the invention in which the second engagement means (whereby the structure can be moved by a therapist) are concealed from view are particularly effective in helping the patient perceive that the damaged limb is at least partly effective in moving the structure in the target direction. Improvement in control of movement of the arm is more readily achieved if the patient is unaware of whether, and to what extent, he or she is being helped by the therapist. The therapist's arm and hand can be concealed by a cover, which can for example be attached to the top of the partition.

One type of rehabilitation therapy aid according to the present invention designed to help exercise a patient's arm has a moveable structure which is free to slide across a support surface. The arm is placed in a recess or sleeve in the moveable structure, or can be secured in a harness which is rigidly connected to the moveable structure. Such a harness can form the first engagement means whereby the structure can be moved by the patient. Alternatively or additionally, the first engagement means can comprise a handle if the patient has sufficient hand control to maintain effective contact with a handle. The form of the handle can be chosen for the patient being treated. For example, some stroke victims have no tight grip and may need a broad shaped handle. Some stroke victims have their hands set in a tight grip and may need a conical handle onto which the patient's hand can be fitted. It may be convenient to have a peg in the structure onto which different handles can be secured. The structure can have means for fixing the handle in varying positions to accommodate patients of differing arm length.

An alternative therapy aid in which the moveable structure is free to move in any direction across a surface above the surface comprises a suspended rod wherein the first and second engagement means are arranged along the rod.

The support surface is preferably flat and smooth so that the rehabilitation aid can be moved easily. For example the moveable structure is usually slideable over a table having a smooth surface. The rehabilitation therapy aid can include a support board across which the moveable structure moves; the moveable structure and the support board can form a transportable rehabilitation therapy aid, for example for use by a therapist visiting patients in their homes.

The second engagement means whereby the structure can be moved by a therapist, or by the patient's stronger arm, usually comprises a handle within a recess or sleeve although a harness is possible. The engagement means whereby the structure can be moved by the therapist is generally separated by a partition from the engagement means whereby the structure can be moved by the patient. The patient's arm and the therapist's arm can be substantially parallel and on either side of the partition. In therapy aids according to the invention designed for solo use by a patient, where the patient's stronger arm engages the second engagement means, the first and second engagement means can be arranged so that the patient's arms are at an angle to each other, which may be a more comfortable position. For example, the first engagement means can be a harness whose position is adjustable to allow a wider angle between the limb of the patient requiring therapy and the limb engaging the second engagement means.

In alternative therapy aids according to the invention the moveable structure can be in two parts linked mechanically. When the therapy aid is used with a therapist, this allows the patient and therapist to be further apart. For example, the two parts can be linked by pivots or sliders. A therapy aid designed mainly for solo use can comprise two articulated bars, the first engagement means being positioned on one of the said bars and the second engagement means being positioned on the other bar, so that when the patient moves the structure towards himself the bars diverge and when the patient moves the structure away from himself the bars converge. Such a therapy aid may also include means for securing the said bars in a position parallel to each other if required when the therapy aid is being used with a therapist.

Normally the sensor or movement detector is such that the movement of the structure can be tracked by the patient so that he or she can see whether the structure is moving in the target direction, and the movement can usually also be tracked by the therapist. In its simplest form the movement detector can consist of marks or lines on the support surface across which the patient tries to move the therapy aid. A rehabilitation therapy aid including a support board may for example include a target pattern visible on the support board. The movement detector can alternatively be a pointer carried by the moveable structure. The pointer can move across a screen in front of the therapy aid, which can be an electronic or non-electronic screen. A therapy aid using a target pattern on the support board or a pointer and a non-electronic screen can be used by patients who do not have computer access.

More usually, the movement detector comprises a device that detects two-dimensional motion relative to a surface and is capable of recording the resulting information in digital form and transmitting it to a computer. The movement detector can be a computer mouse fixed into the moveable structure. Alternatively the moveable structure may have in its base one or more light-emitting diodes (LEDs) and an imaging array of photodiodes to detect movement relative to the underlying surface, that is the base of the moveable structure can include the electro-optical system used in an optical mouse. When the electro-optical system is thus built into the moveable structure, the handles for moving the structure can also control the programmes shown on the monitor screen; that is to say either or both of the handles for the therapist and patient to move the structure can act in a similar way to the buttons of a computer mouse.

A rehabilitation therapy aid according to the invention whose movement detector comprises a computer mouse or similar electronic optical system is generally used with a monitor screen programmed to display the movements of the structure tracked by the mouse. The rehabilitation therapy aid may include a monitor screen programmed to display the movements of the structure tracked by the device that detects two-dimensional motion relative to a surface. It may however not always be necessary to transport a monitor screen with the therapy aid; if a patient has a home computer that can be programmed to display the movements detected.

The movement detector can alternatively comprise a switch built into the framework of the moveable structure. A switch movement detector may be advantageous when the therapy aid is designed to aid movement of a limb about a joint.

In use, the patient tries to move the moveable structure in an indicated direction. For example, the patient moves the structure so that a cursor indicating the position of the moveable structure moves towards a target position on the screen. The therapist has his or her hand or arm in contact with the engagement means. If the patient is successful in moving to the target position, the therapist does not apply any force. If the therapist senses that the patient is having great difficulty in moving the moveable structure in the indicated direction, the therapist moves the structure in that direction, either gently or more firmly as necessary. As the patient's arm is secured to the moveable structure, his or her arm moves in the indicated direction. The patient's arm movement is essentially the same as the movement made by the therapist, so that the patient voluntarily or involuntarily mimics the therapist's arm movement. The therapy aid of the invention can thus be used with patients who initially have no movement of the limb being exercised. The exercise is generally repeated many times. As the exercise is repeated, it is usually found that the patient's control of the arm and hand movement improves to some extent, so that the degree of firmness of physical guidance applied by the therapist can decrease with repetition.

If a patient can easily move the moveable structure so that the cursor on the screen reaches a target position, more difficult exercises can be programmed. For example, the structure may be required to move so that the cursor follows an indicated convoluted path involving changes of direction. A simple video game can be programmed so that the patient is required to attempt control of timing of the movements.

Alternatively, the cursor can be replaced by pictures, words and/or colours, to make exercises which can help in memory return to help conditions such as aphasia. Sounds can also be used. Thus in one therapy method the target direction is indicated by a picture, word and/or colour on the monitor screen and the target picture, word and/or colour is named to the patient. For example, there would be numerous pictures of fruit around the screen, the cursor appears in the middle as the text 'APPLE', a voice says the word 'apple' and the patient has to move the cursor to the apple picture. The exercise can be repeated with a different fruit, or different topic. This way exercises can help with rebuilding the neurological paths for physical activity and help exercise memory functions at the same time.

Generally, the therapist remains in contact with the second engagement means so that the therapist can help and guide the movement attempted by the patient. Alternatively, the patient's stronger limb remains in contact with the second engagement means. While the target-oriented movements required by the exercises may not be of direct practical use, repetition of the exercises helps in rebuilding neurological pathways involved in muscle control so that the patient can eventually improve at practical tasks such as dressing, eating or writing.

The invention will now be described with reference to the accompanying drawings, of which FIG. 1 is a perspective view of a therapy aid according to the invention for arm movement;

Figure 1:
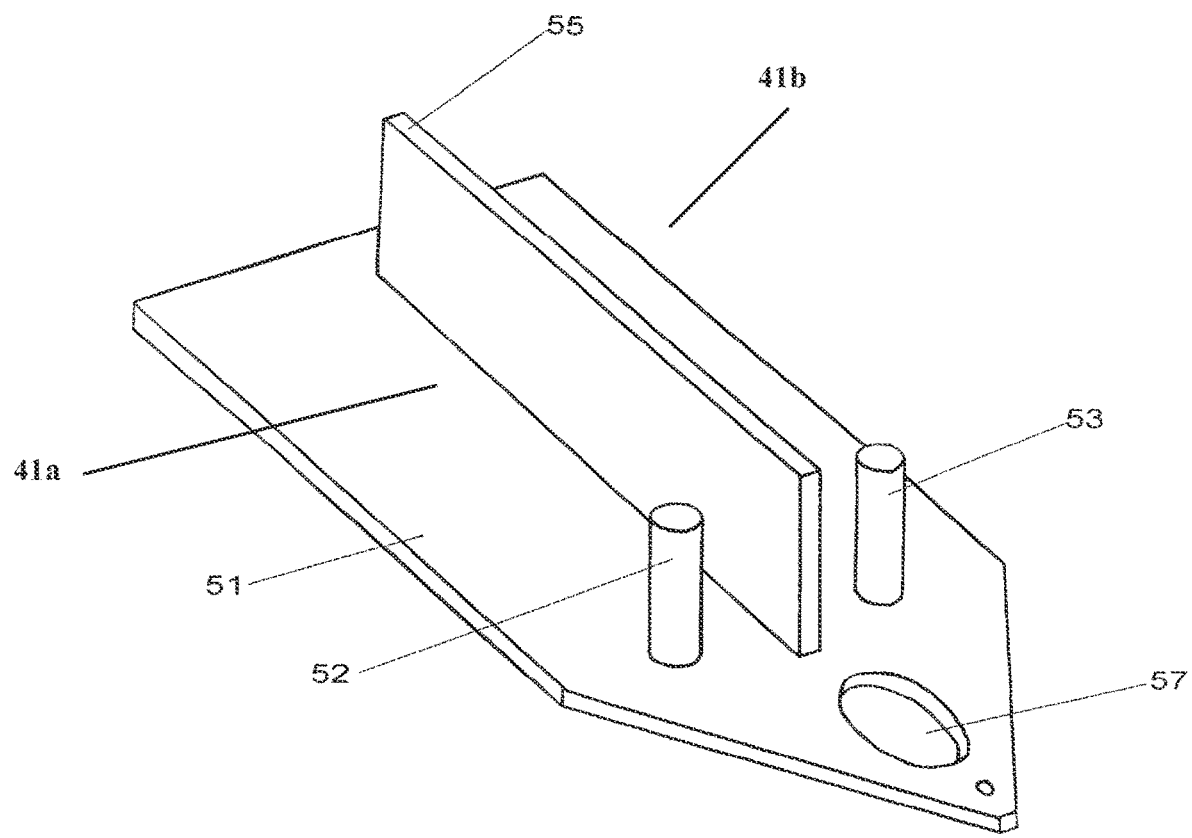

The therapy aid of FIG. 1 comprises a base 51 carrying a first support or a handle 52 for engagement by the patient (if the patient needs therapy exercise of the left arm) and a second support or a handle 53 for engagement by the therapist. The therapy aid can alternatively be used for exercise of the right arm in which case handle 53 is for engagement by the patient and handle 52 for engagement by the therapist. The therapy aid has a partition or a plate 55 separating the patient's arm from the therapist's arm. The base 51, handle 52, and partition or plate 55 define a first receptacle 41a on a first side of the partition or plate 55, wherein the first receptacle is configured to receive the patient's arm. The base 51, handle 53, and partition or plate 55 define a second receptacle 41b configured to receive another arm of the patient or an arm of the therapist. In aspects, the first and second receptacle 41a, 41b, may be defined by the base 51 and their respective handles 52, 53, or by the base 51 and respective sides of the partition or plate 55. An aperture 57 in the base can be fitted with a computer mouse as a movement detector. The therapy aid of FIG. 1 is slideable over a flat surface such as a tabletop. Such a slideable device allows freer movement in two dimensions than a slider device as described in DE-OLS-202004015122.

Figure 2:
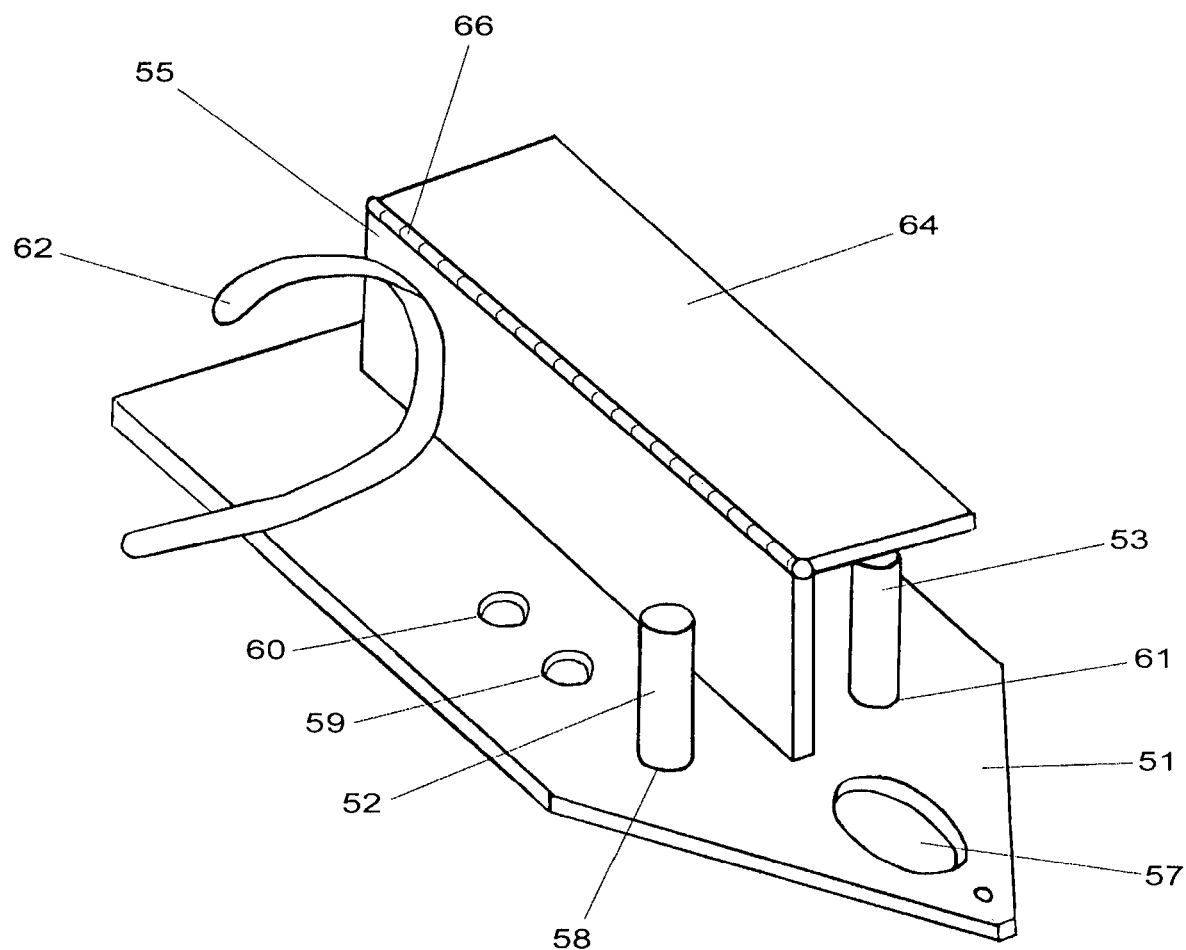
FIG. 2 is a perspective view of a therapy aid similar to that shown in FIG. 1 further comprising means for concealing the therapist's arm.

In the therapy aid of FIG. 2, a cover plate 64 is joined to partition 55 so that the patient can not see the therapist's hand and arm motion. The cover plate 64 is joined by hinge 66 so that the position of the cover plate can be moved when a patient needs exercise of the right arm.

In the therapy aid of FIG. 2, handle 52 is fixed in an aperture 58 in base 51 but can be moved to be fixed in alternative positions defined by apertures 59, 60 in base 51. Handle 53 is fixed in aperture 61 in base 51 and can be fixed in alternative positions defined by apertures not seen in FIG. 2. The therapy aid can thereby more easily accommodate patients of different arm size. An alternative means of adjustability for arm length is a track along base 51 in which the handle 52 can be fixed in varying positions. A strap 62 is fixed to the base 51 and to the partition 55 to secure the patient's arm to the therapy aid. A similar strap (not shown) can be fixed on the other side of the partition for use when the patient is exercising the right arm.

Figure 3:
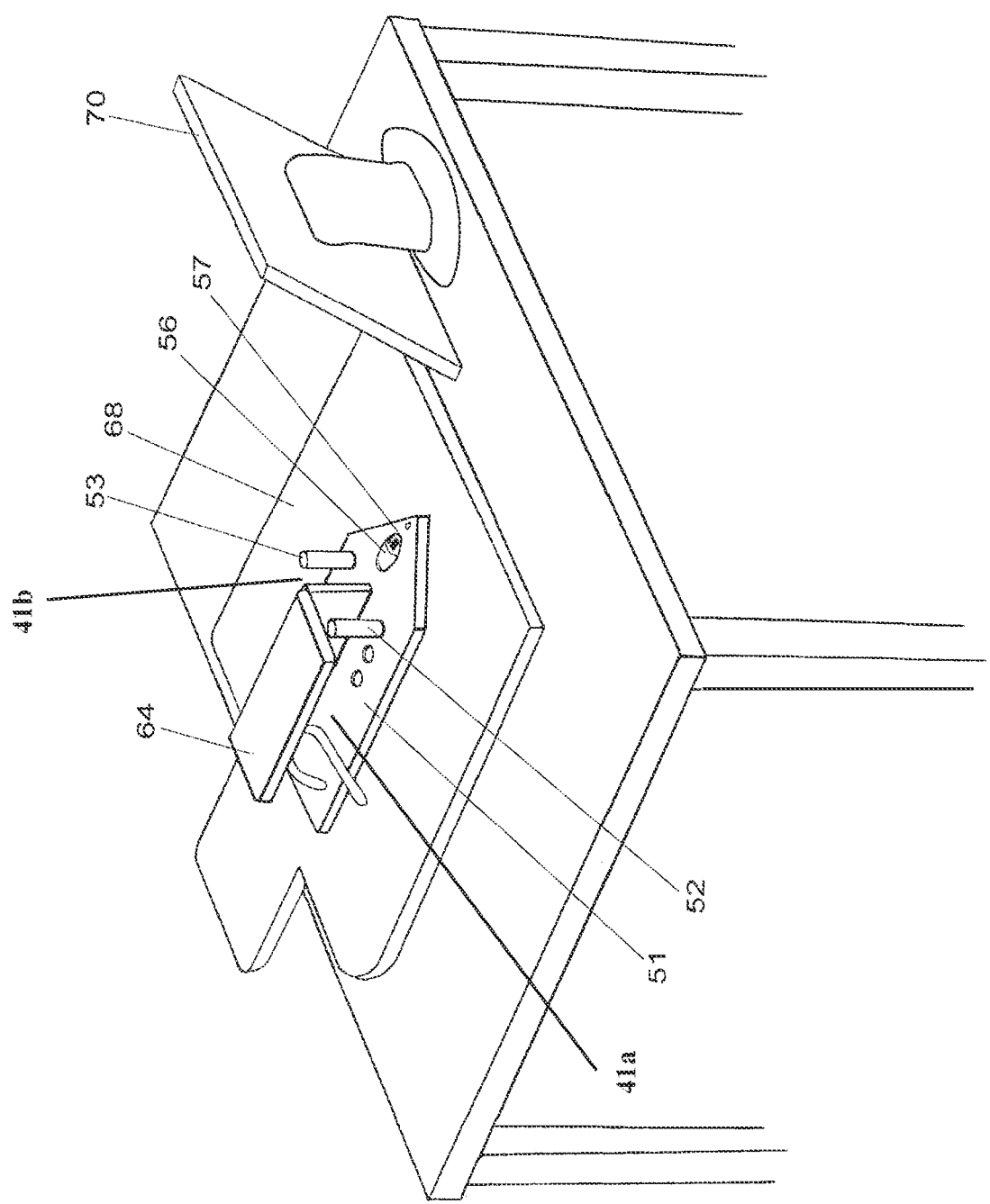
FIG. 3 is a perspective view of a therapy aid similar to that shown in FIG. 2 further comprising a support board and monitor screen.

FIG. 3 shows the therapy aid with a support board 68 and a monitor screen 70. The base 51 of the therapy aid can be moved by sliding across the support board 68 in two dimensions. A computer mouse 56 is located in aperture 57 of base board 51. It will be understood that mouse 56 and aperture 57 can be replaced by an electro-optical system incorporated in the base 51. In FIG. 3 the cover plate 64 has been moved for a patient needing exercise of the right arm so that handle 53 is for engagement by the patient and handle 52 is for engagement by the therapist. In aspects, the first and second receptacles 41a, 41b, are each further defined by the cover plate 64.

Figure 4:
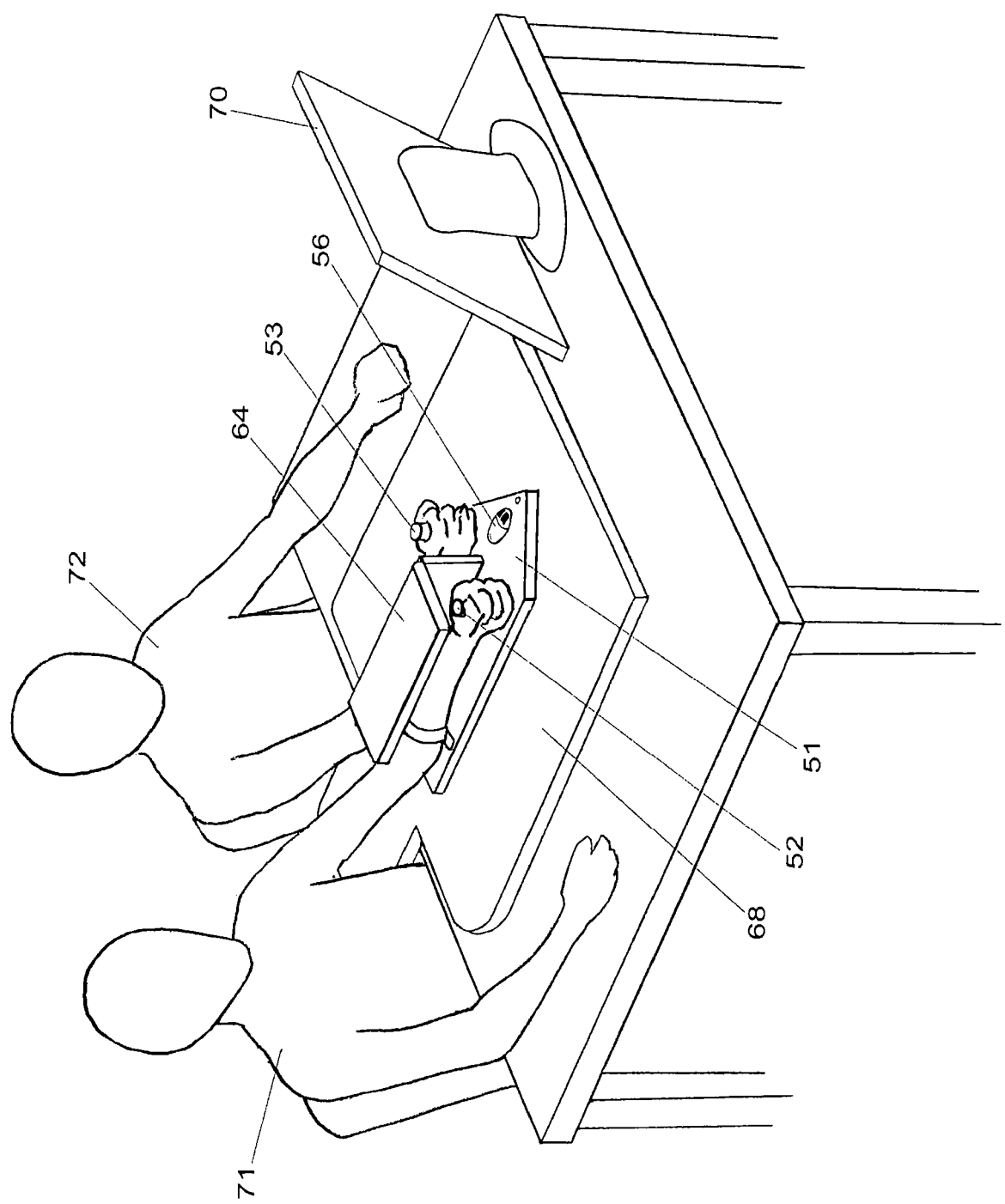
FIG. 4 is a perspective view showing the therapy aid of FIG. 3 in use.

FIG. 4 shows the therapy aid of FIG. 3 in use exercising a patient's right arm, with a therapist 71 holding handle 52 aiding a patient 72 holding handle 53.

Figure 5:
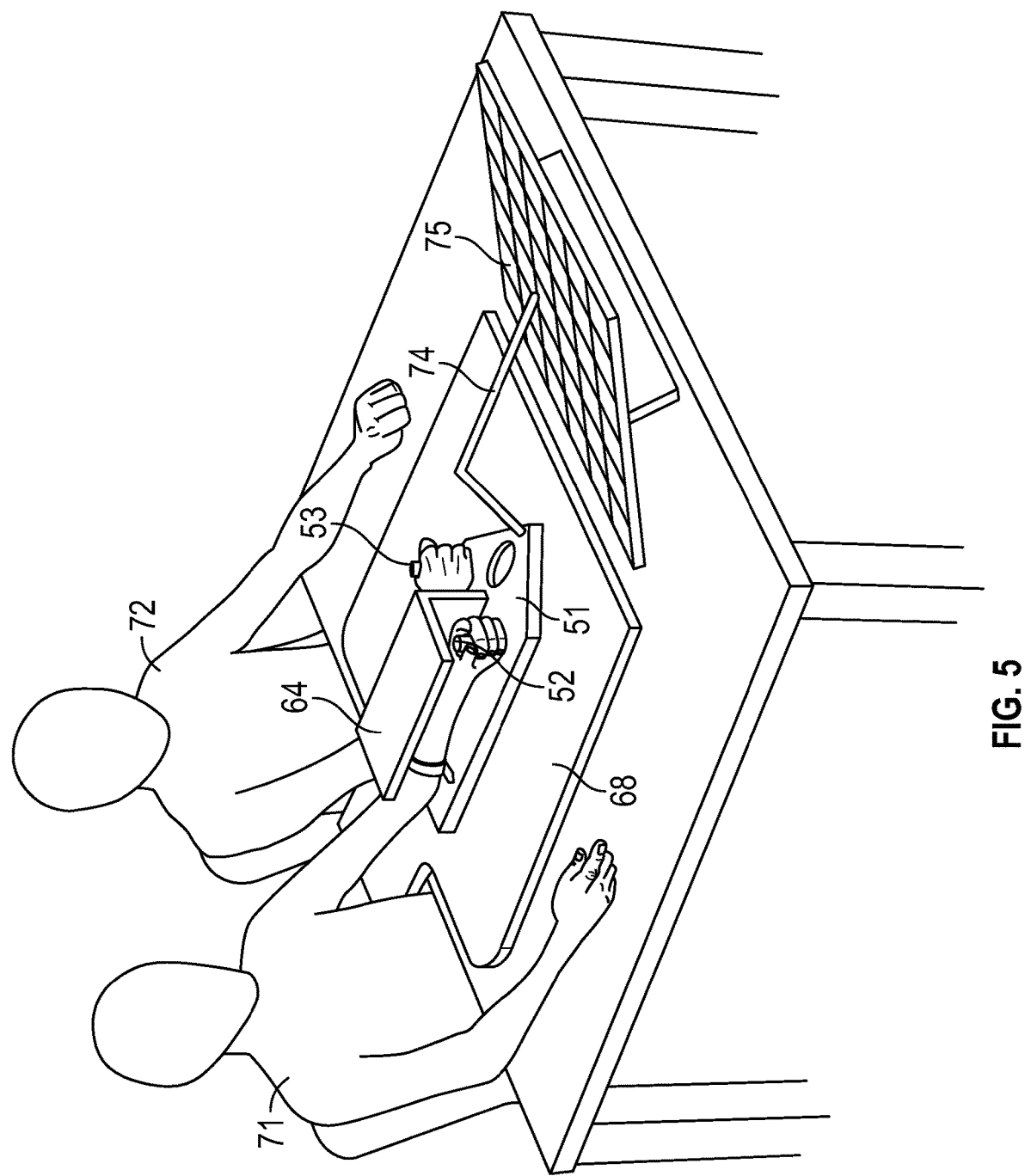
FIG. 5 is a perspective view of a therapy aid similar to the aid of FIGS. 1 to 4 having an alternative movement detector.

FIG. 5 shows a therapy aid similar to the aid of FIGS. 1 to 4 with identical parts being numbered identically. The therapy aid of FIG. 5 does not use a mouse but has a pointer 74 mounted on the base 51. The remote end of the pointer 74 moves across a screen 75 having a target pattern to detect movement. The therapy aid of FIG. 5 does not require computer access, although it can be used with a computer screen.

Figure 6:
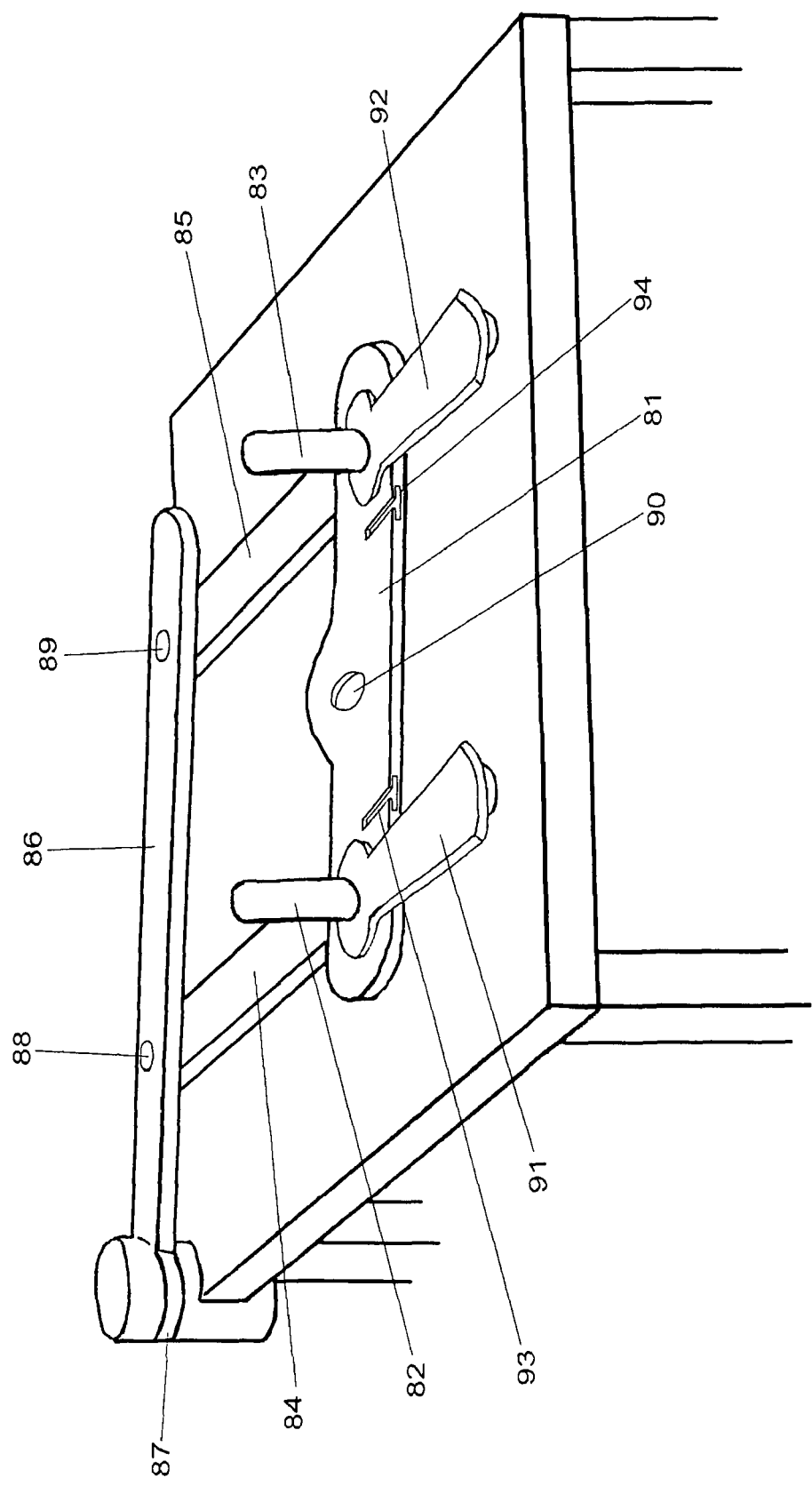
FIG. 6 is a perspective view of an alternative therapy aid according to the invention for arm movement.

The therapy aid of FIG. 6 comprises a base 81 carrying handles 82 and 83 for engagement by the patient and therapist, The base is linked by struts 84, 85 to an arm 86 which can rotate about a pivot 87. The struts 84, 85 are linked to arm 86 by pivots 88, 89 so that the therapy aid can be moved in two dimensions. The base 81 has an aperture 90 for a mouse; alternatively an electro-optical position detector can be built into the base 81 or a pointer as shown in FIG. 5 can be attached to the base 81. The handles 82 and 83 can be sufficiently far apart that the patient and therapist can if desired comfortably sit side by side each using the right arm (or each using the left arm). Each handle 82, 83 has an associated arm support 91 and 92 respectively. The base 81 has profiled slots 93 and 94 into which a cover can be fitted, as shown in FIG. 7.

Figure 7:
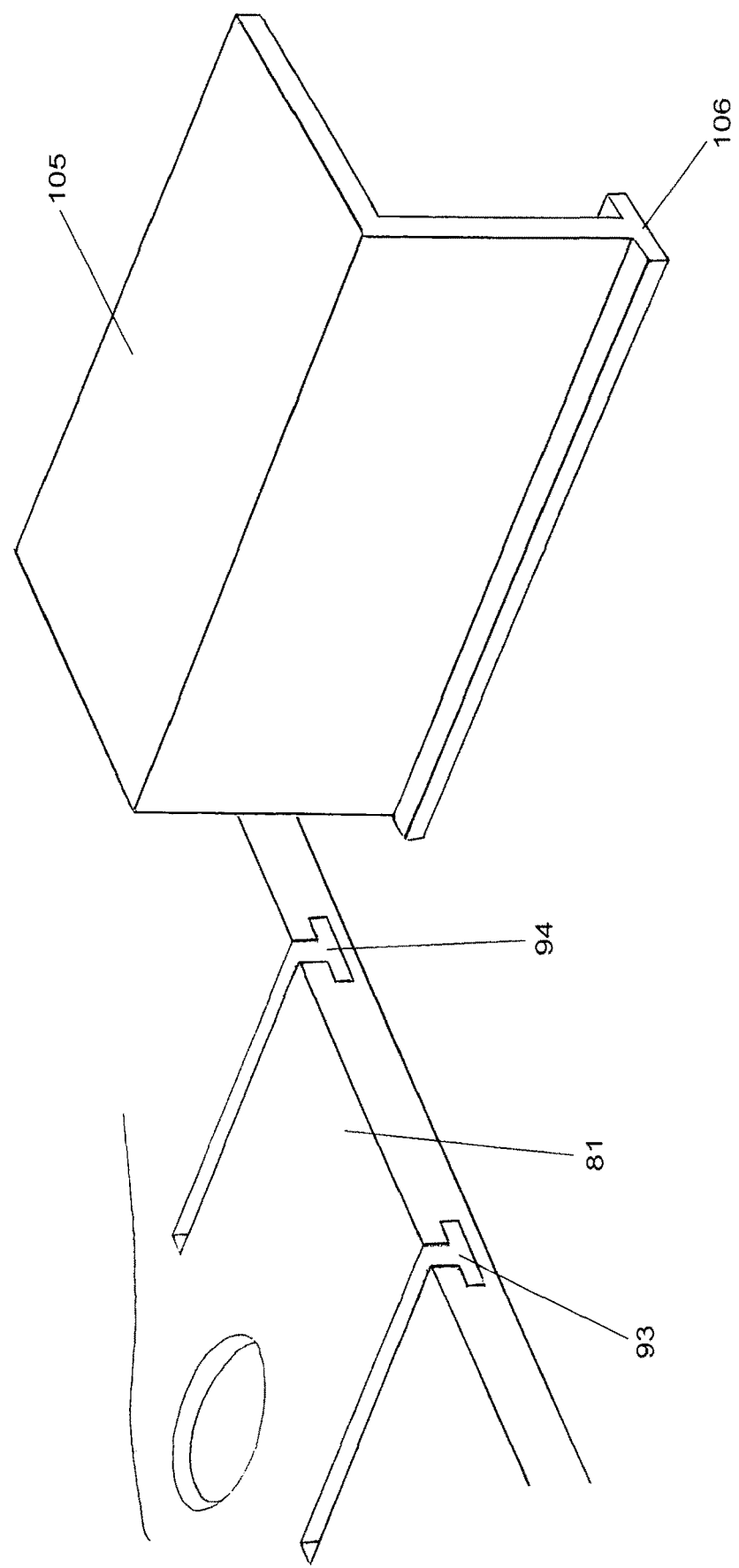
FIG. 7 is a perspective view of a cover that can be fitted to the therapy aid of FIG. 6.

The cover 105 shown in FIG. 7 has a profiled base 106 which can fit into slot 93 or 94 of the aid of FIG. 6. The cover 105 is reversible so that it can conceal the therapist's arm whichever side of the therapy aid the therapist is sitting.

While an optical mouse is suitable for detection of movement in two dimensions, the movement detector can alternatively be a 3-D mouse which can detect movements away from the support surface such as lifting of the hand or lifting of a moveable structure away from a support surface in addition to movement in two dimensions across the support surface. A 3-D mouse can be worn on the patient's hand or can be attached to the structure so that it moves with the patient's hand and can function through ultrasound.

Although the invention has been described mainly with reference to rehabilitation of arm and hand movements, a rehabilitation therapy aid according to the present invention can be designed to help exercise a patient's leg. For this purpose the patient's leg can be secured in a harness which allows the leg to move flexibly, but is rigidly attached to a parallel harness in which the therapist's leg can be secured. Movement of the patient's leg, for example raising of the foot, altering the angle of the knee or of the ankle, or a kicking movement, can be detected by a 3-D mouse worn by the patient or by switches or electronic movement detectors in the framework of the structure.

Figure 8:
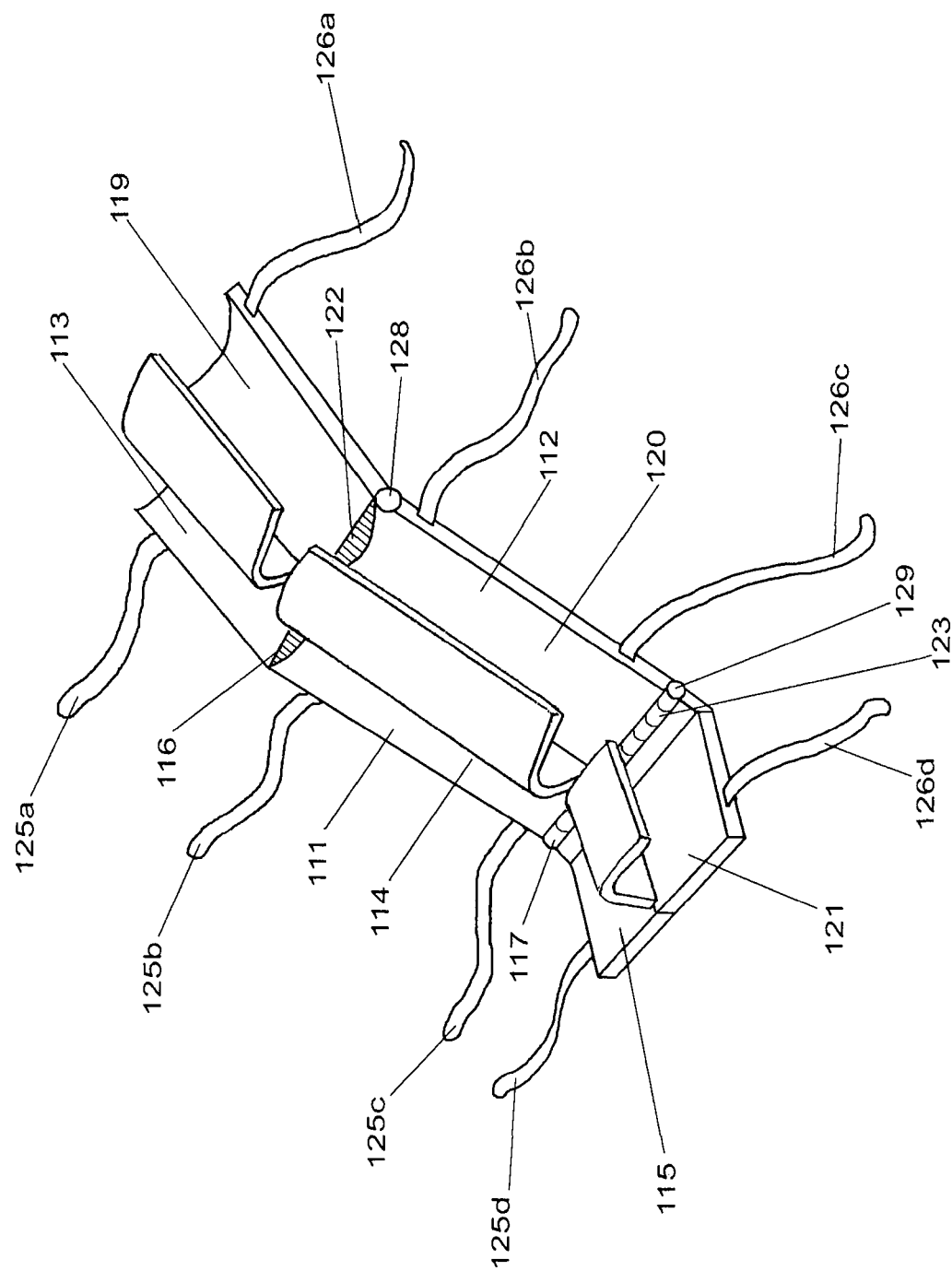
FIG. 8 is a perspective view of a therapy aid according to the invention for leg movement.
Figure 9:
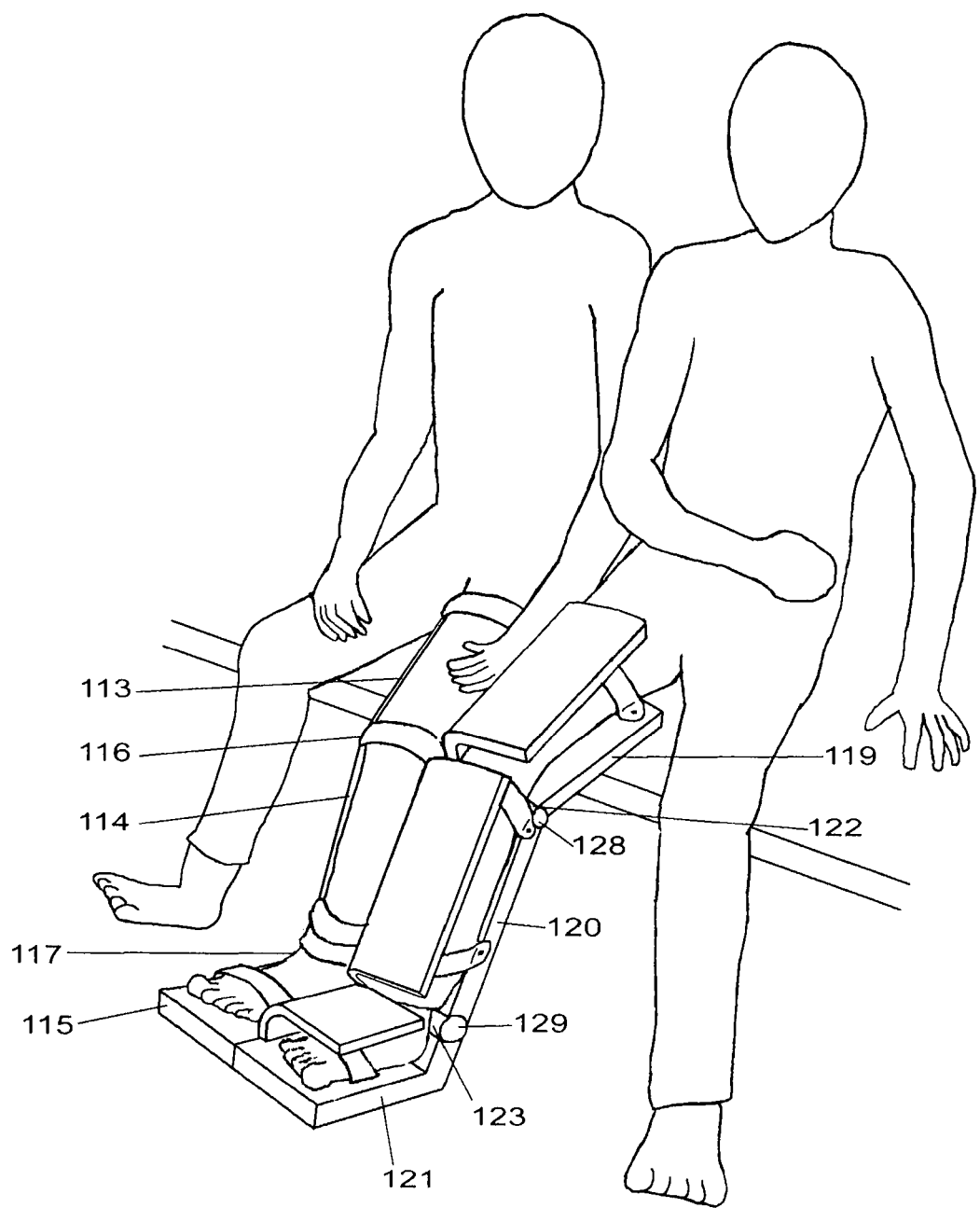
FIG. 9 is a perspective view of the therapy aid of FIG. 8 in use.

The therapy aid of FIGS. 8 and 9 comprises a leg support 111 for the patient and a leg support 112 for the therapist. The leg support 111 comprises a substantially rigid thigh support 113, a substantially rigid calf support 114 and a substantially rigid foot support 115. The leg support 111 has a flexible knee portion 116 and a flexible ankle portion 117. Similarly the leg support 112 has substantially rigid thigh, calf and foot supports 119, 120 and 121 respectively and flexible knee and ankle portions 122 and 123 respectively. The therapy aid is provided with straps 125a to 125d for securing the patient's leg to the therapy aid, and straps 126a to 126d for securing the therapist's leg to the therapy aid. A partition can be positioned between the leg support 111 and the leg support 112; such a partition can optionally have a fabric cover attached which would conceal movement of the therapist's leg. As described, FIGS. 8 and 9 show a therapy aid for exercising a patient's left leg, but the positions of the patient and therapist can be reversed if exercise of the right leg is required.

In use, the therapist can lead the patient in exercises such as a kicking exercise involving flexing of the knee and possibly also the ankle, or an exercise in raising or lowering the foot involving flexing of the ankle. The flexible knee portion 116 and flexible ankle portion 117 contain switches 128 and 129 respectively to detect whether the patient has flexed his knee or ankle by the targeted amount. The switches can alternatively be mounted in the centre of the structure between the patient's leg and therapist's leg. Alternatively movement of the patient's leg can be detected by a 3-D mouse.

Figure 10:
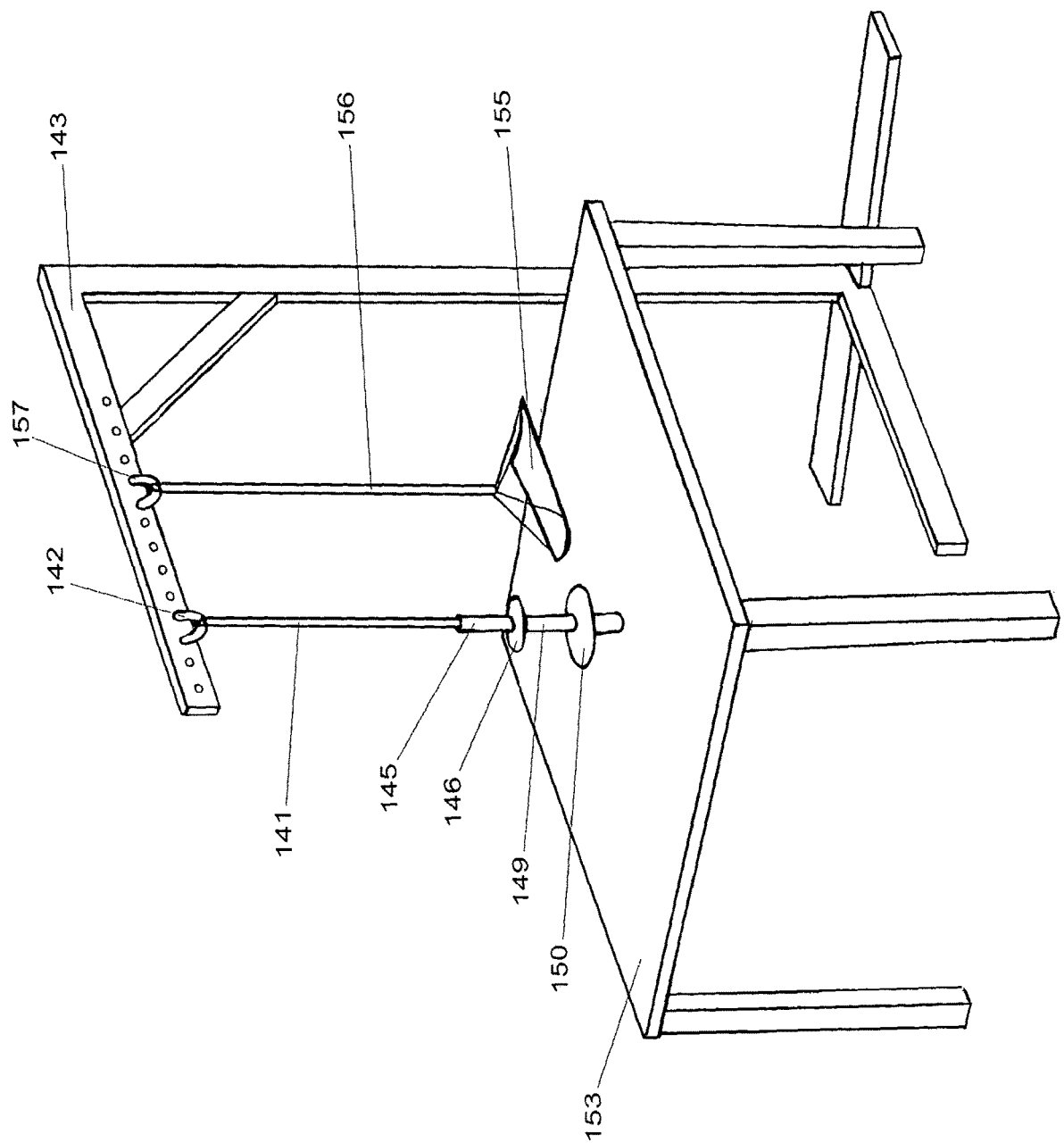
FIG. 10 is a perspective view of a further alternative therapy aid according to the invention for arm movement.
Figure 11:
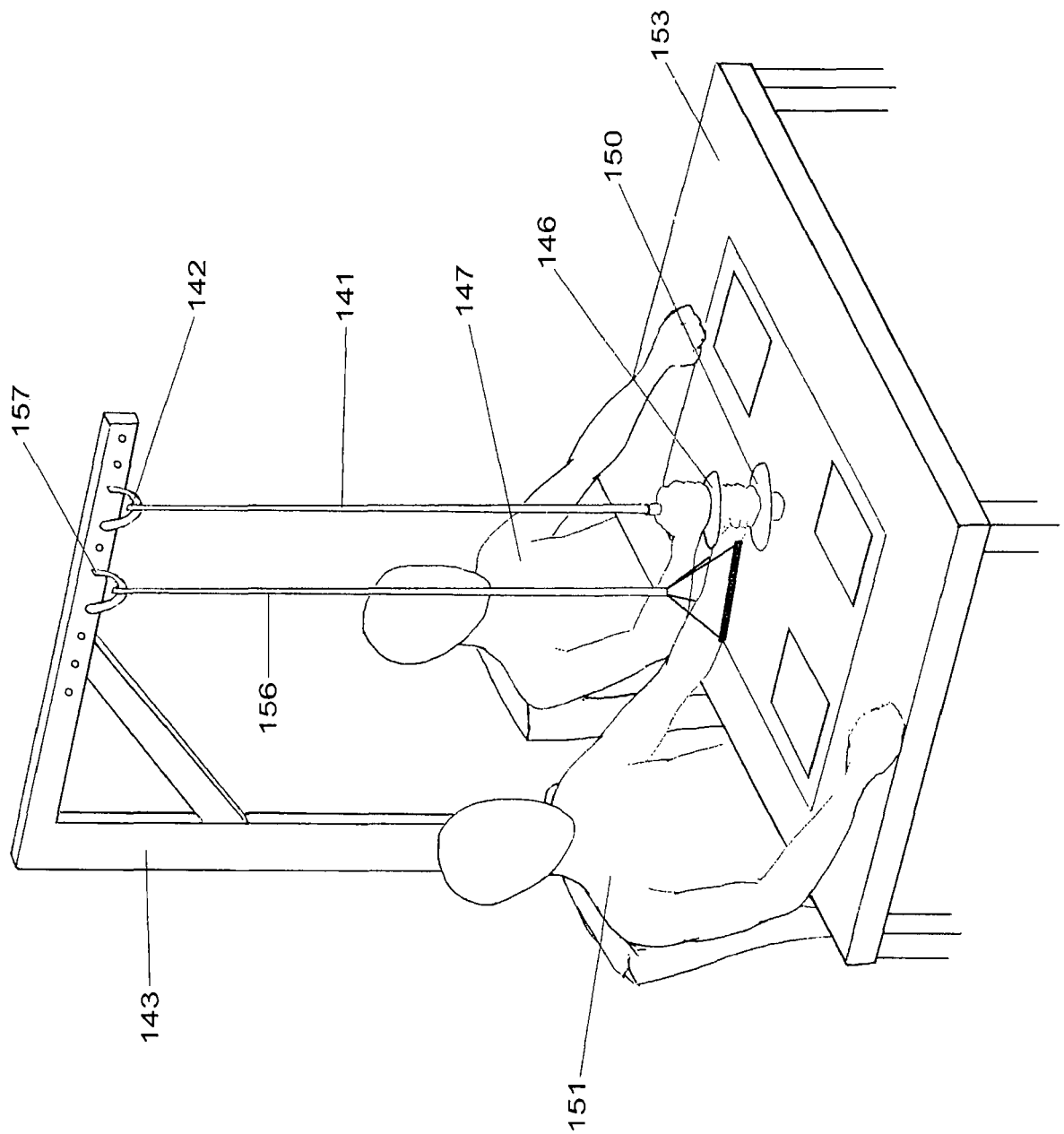
FIG. 11 is a perspective view showing the therapy aid of FIG. 10 in use.

The therapy aid of FIGS. 10 and 11 comprises a rod 141 suspended from a support 142 fixed in a gibbet 143. Arranged along the rod are a handle 145 with hand rest 146 for engagement by a therapist 147 and a handle 149 with hand rest 150 for engagement by the patient 151. The rod 141 can be moved essentially in two dimensions by the patient and/or the therapist over the surface of a table 153. Movement can be detected by a target on the table 153 as indicated in FIG. 11. Alternatively the lower tip of rod 141 can comprise an electro-optical movement detector.

An arm support 155 for the patient's arm can be positioned level with handle 149 as shown in FIG. 10. The arm support 155 is slung from a rope or wire 156 suspended from a support 157 in gibbet 143. The support 157 can be fixed in different positions along gibbet 143 to accommodate patients of differing arm length.

Figure 12:
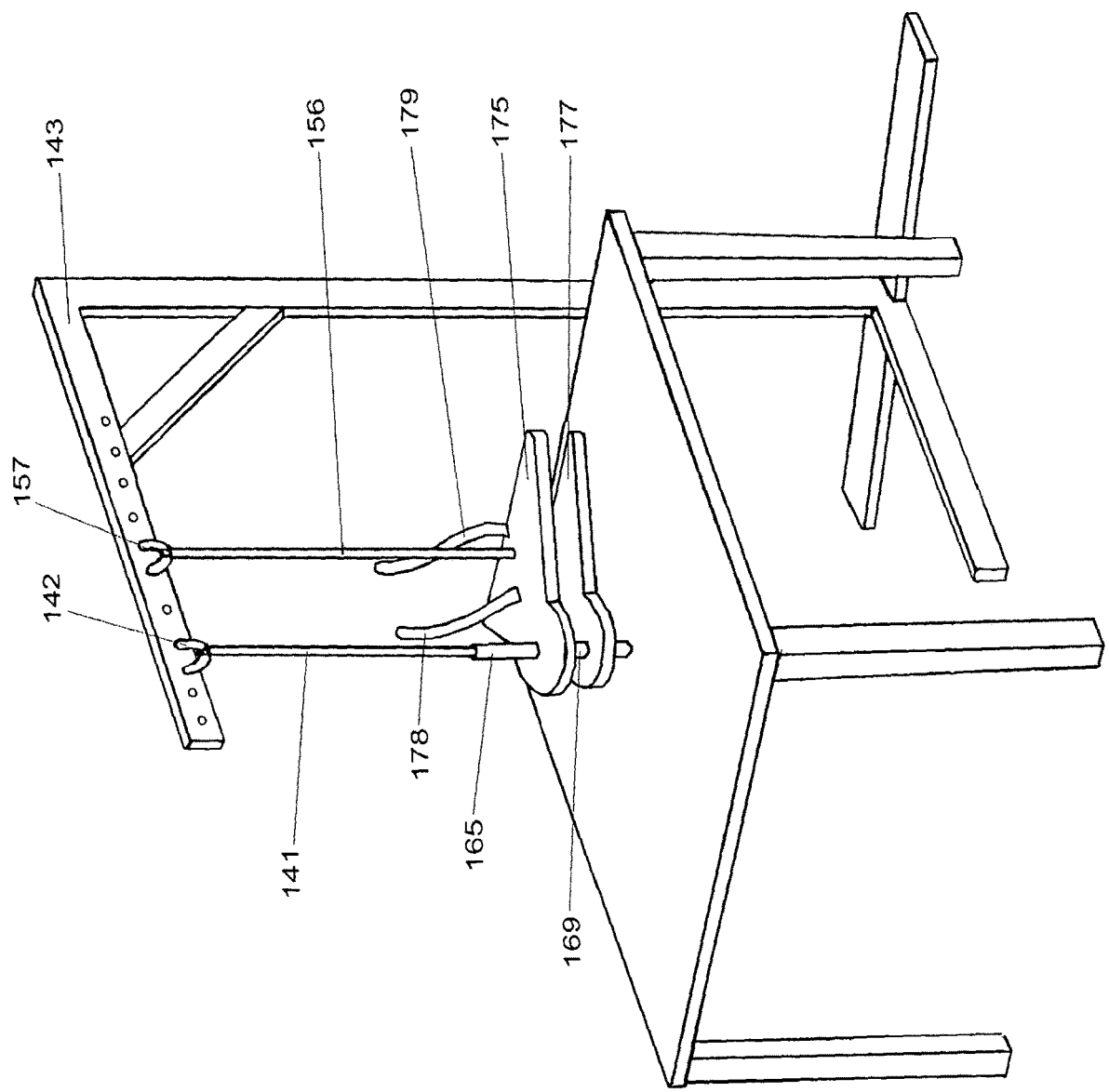
FIG. 12 is a perspective view of a therapy aid similar to that shown in FIG. 10 further comprising means for concealing the therapist's arm.
Figure 13:
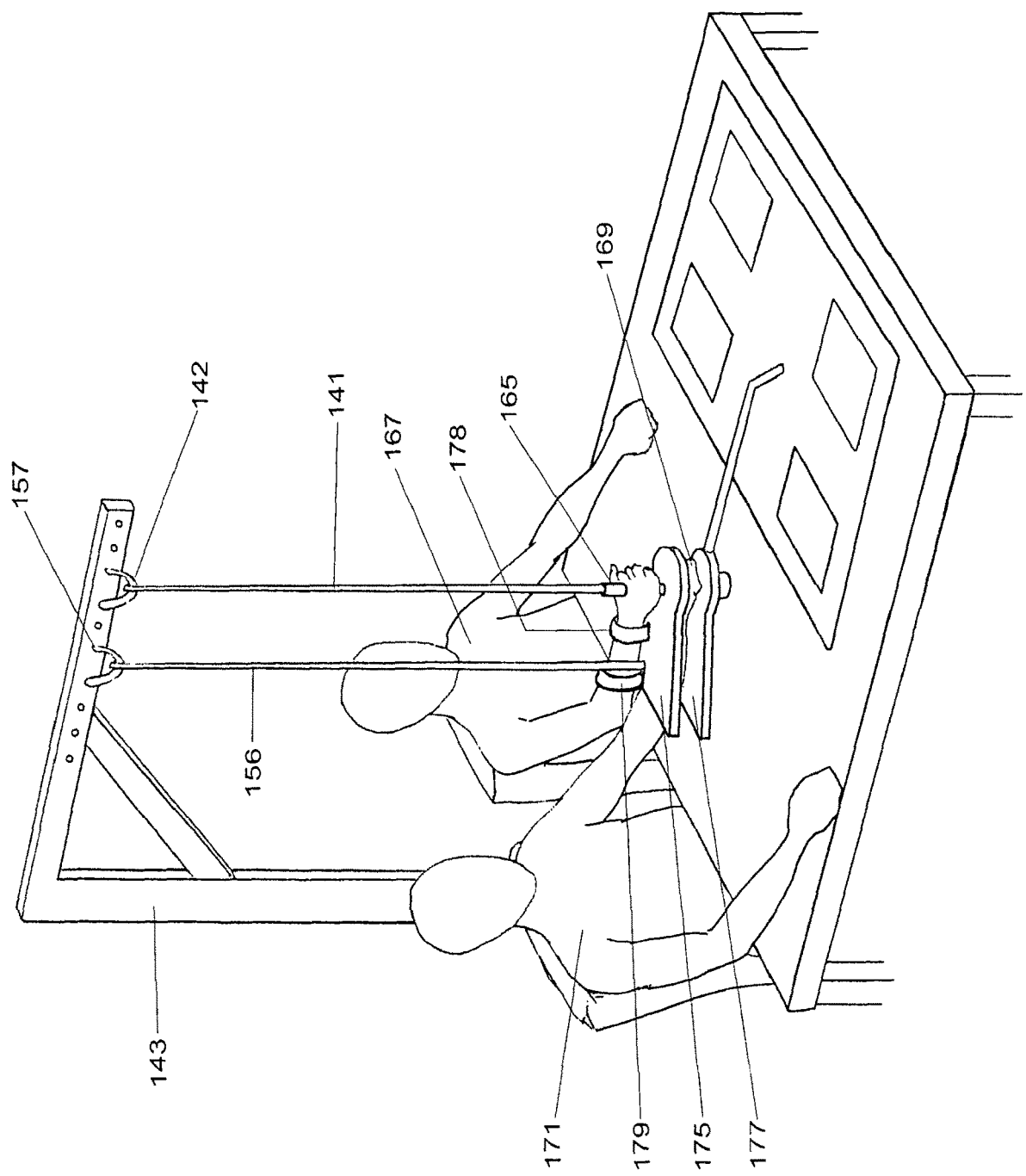
FIG. 13 is a perspective view showing the therapy aid of FIG. 12 in use.

In the therapy aid of FIGS. 12 and 13 the handle 165 for engagement by the patient 167 is positioned above the handle 169 for engagement by the therapist 171. The hand rest for the patient is integral with the arm support 175. The handle 169 has a similar hand rest integral with arm support 177. The arm support 175 has straps 178, 179 for securing a patient's arm to the support 175. The extended arm support 175 incorporating the hand rest conceals the therapist's arm from the patient's view.

Figure 14:
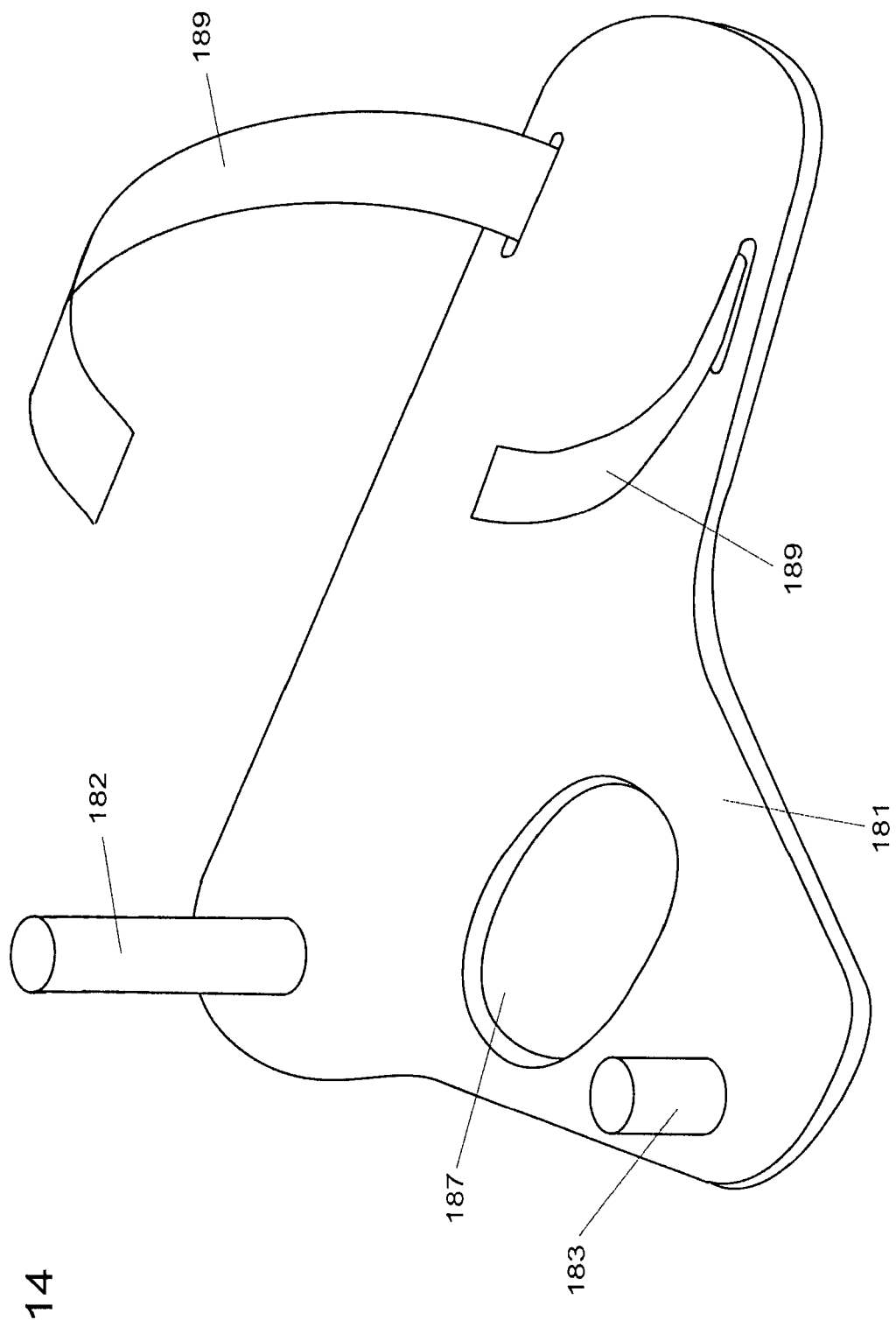
FIG. 14 is a perspective view of an alternative therapy aid according to the invention designed primarily for solo use by a patient.

The therapy aid of FIG. 14 comprises a base 181 carrying a handle 182 for engagement by the patient's hand and arm needing therapy exercise and a handle 183 for engagement by the patient's stronger hand and arm (or alternatively for engagement by a therapist). The handle 182 can be shaped to suit the patient's grip. The handle 183 can be smaller than the handle 182, as shown, although this is not necessary. An aperture 187 in the base 181 can be fitted with a computer mouse as a movement detector. A strap 189 is fixed to the base 181 to secure the patient's arm needing exercise to the therapy aid. The version of the therapy aid shown in FIG. 14 is for a patient whose right arm needs therapy exercise. A version of the therapy aid which is a mirror image of that shown in FIG. 14 can be produced for a patient whose left arm needs therapy exercise. The base 181 can have a partition and a cover concealing the handle 183, if desired.

Figure 15:
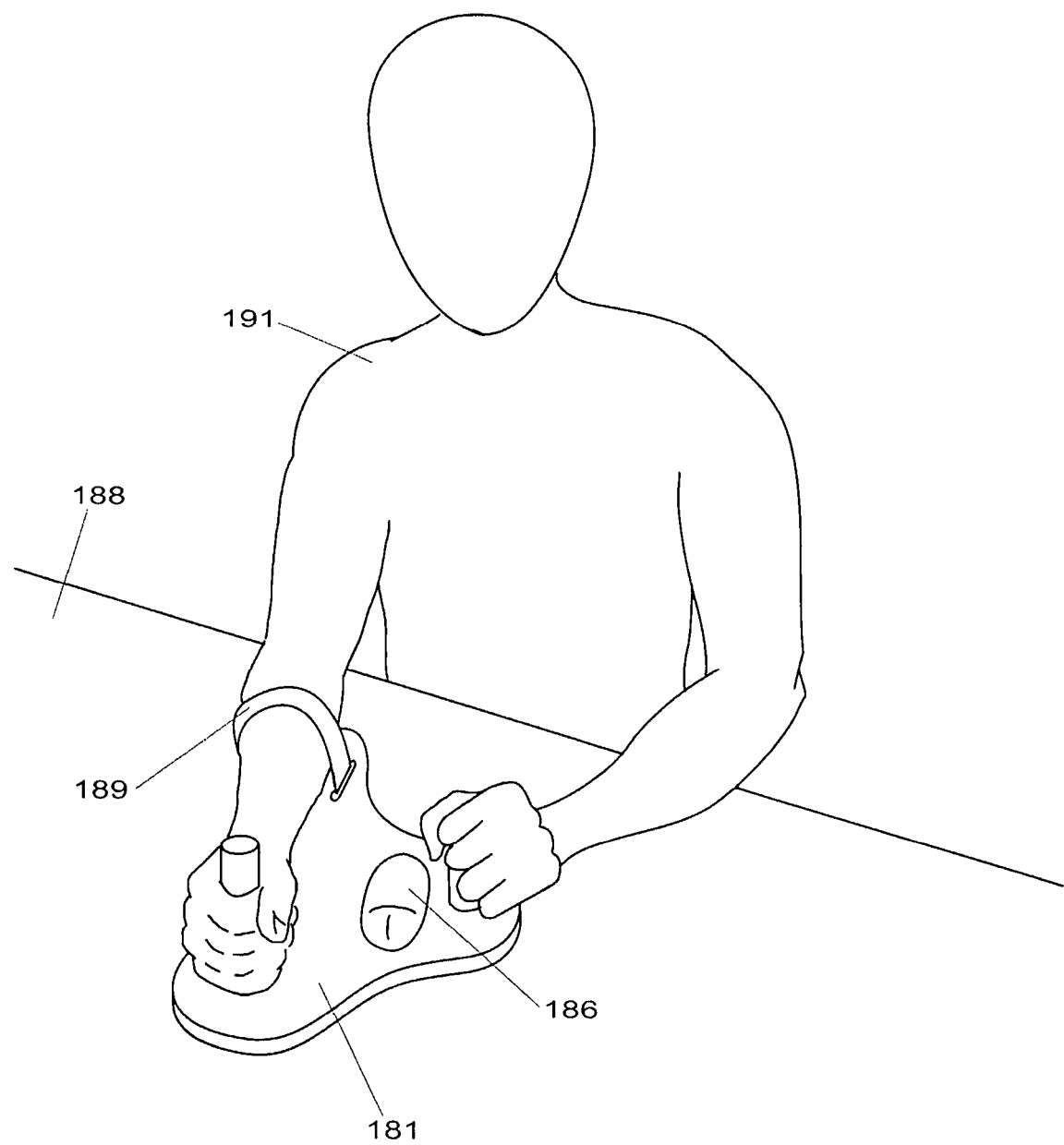
FIG. 15 is a perspective view showing the therapy aid of FIG. 14 in use.

FIG. 15 shows the therapy aid of FIG. 14 in use by a patient 191. The base 181 of the therapy aid can be moved by sliding across the support board 188 in two dimensions. A computer mouse 186 is located in aperture 187 of base board 181.

Figure 16:
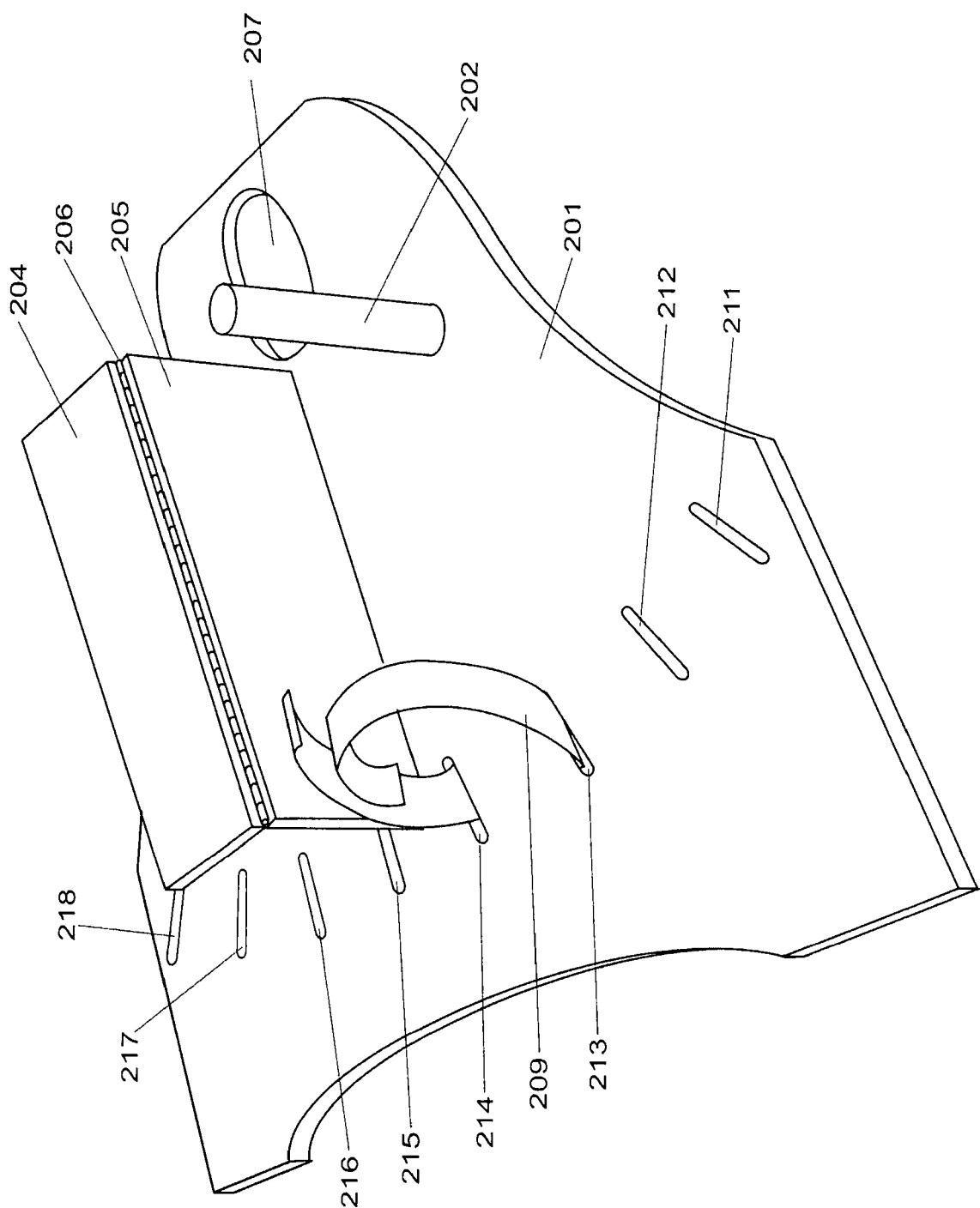
FIG. 16 is a perspective view of a further alternative therapy aid according to the invention.
Figure 17:
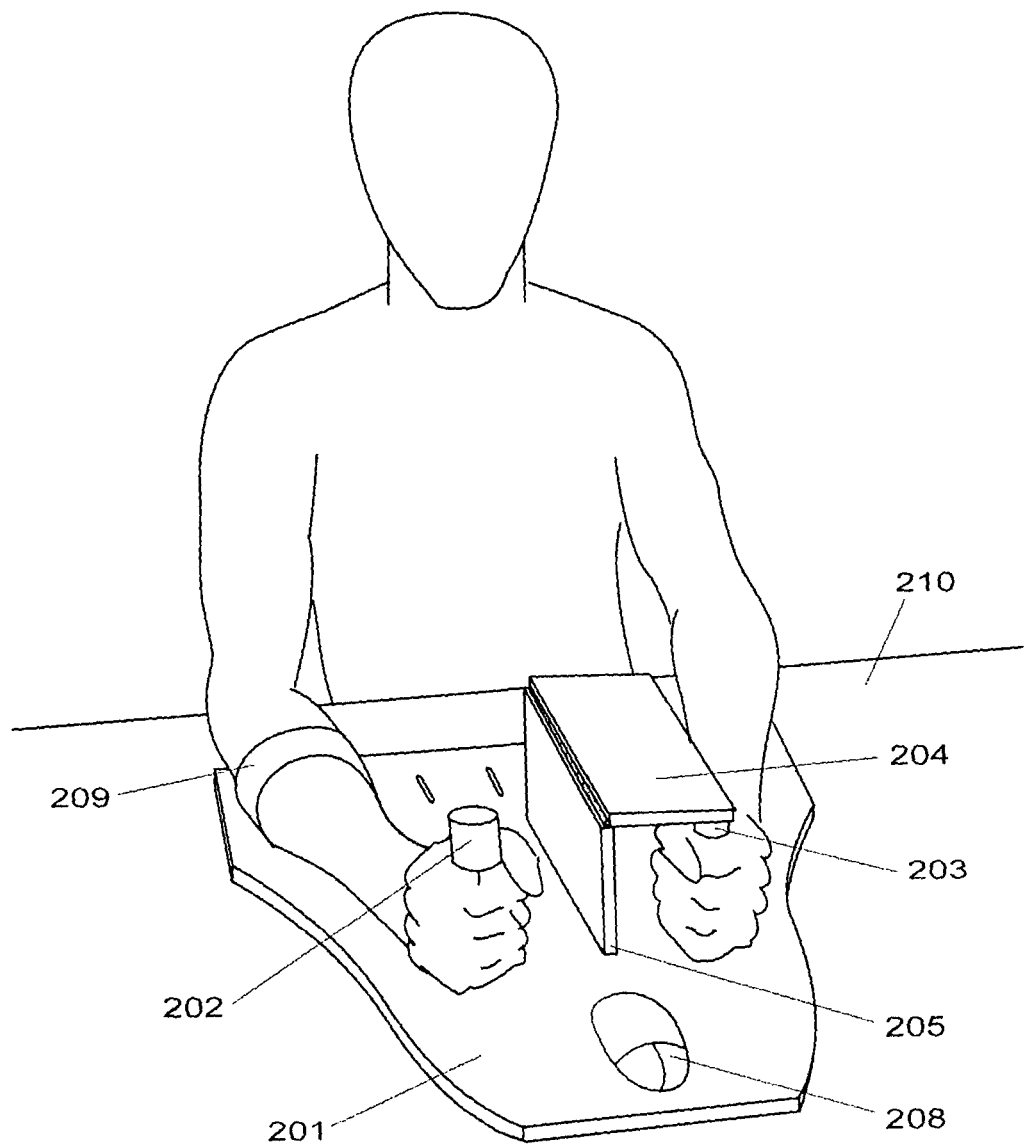
FIG. 17 is a perspective view showing the therapy aid of FIG. 16 in solo use by a patient.

The therapy aid of FIG. 16 comprises a base 201 carrying a handle 202 and a handle 203 (seen in FIG. 17). The handles 202 and 203 are usually similar so that either can be engaged by the patient's hand and arm needing therapy and either can be engaged by a therapist or by the patient's stronger hand and arm. The therapy aid has a partition 205 which can separate the patient's arm from a therapist's arm, A cover plate 204 is joined to partition 205 by hinge 206 so that the position of the cover plate can be moved. An aperture 207 in the base 201 can be fitted with a computer mouse 208 as a movement detector. A strap 209 is capable of being fixed to the base 201 to secure the patient's arm needing exercise to the therapy aid. The base 201 has a series of slots 211 to 218 arranged so that the strap 209 can be secured in position by passing through adjacent slots.

In FIG. 16, the strap 209 is shown passing through slots 213 and 214. The therapy aid is arranged to exercise a patient's left arm with help from a therapist. The patient and therapist can sit side by side as shown in FIG. 4 and the cover 204 conceals the therapist's hand and arm.

In FIG. 17 the patient is shown moving the therapy aid of FIG. 16 across a surface 210. In FIG. 17 the strap 209 is shown passing through slots 211 and 212 of FIG. 16. The therapy aid is arranged to exercise a patient's right arm with help from the patient's stronger left arm. The use of slots 211 and 212 allows the patient's arms to be at an angle to each other, which is more comfortable for solo use than use with arms parallel.

Figure 18:
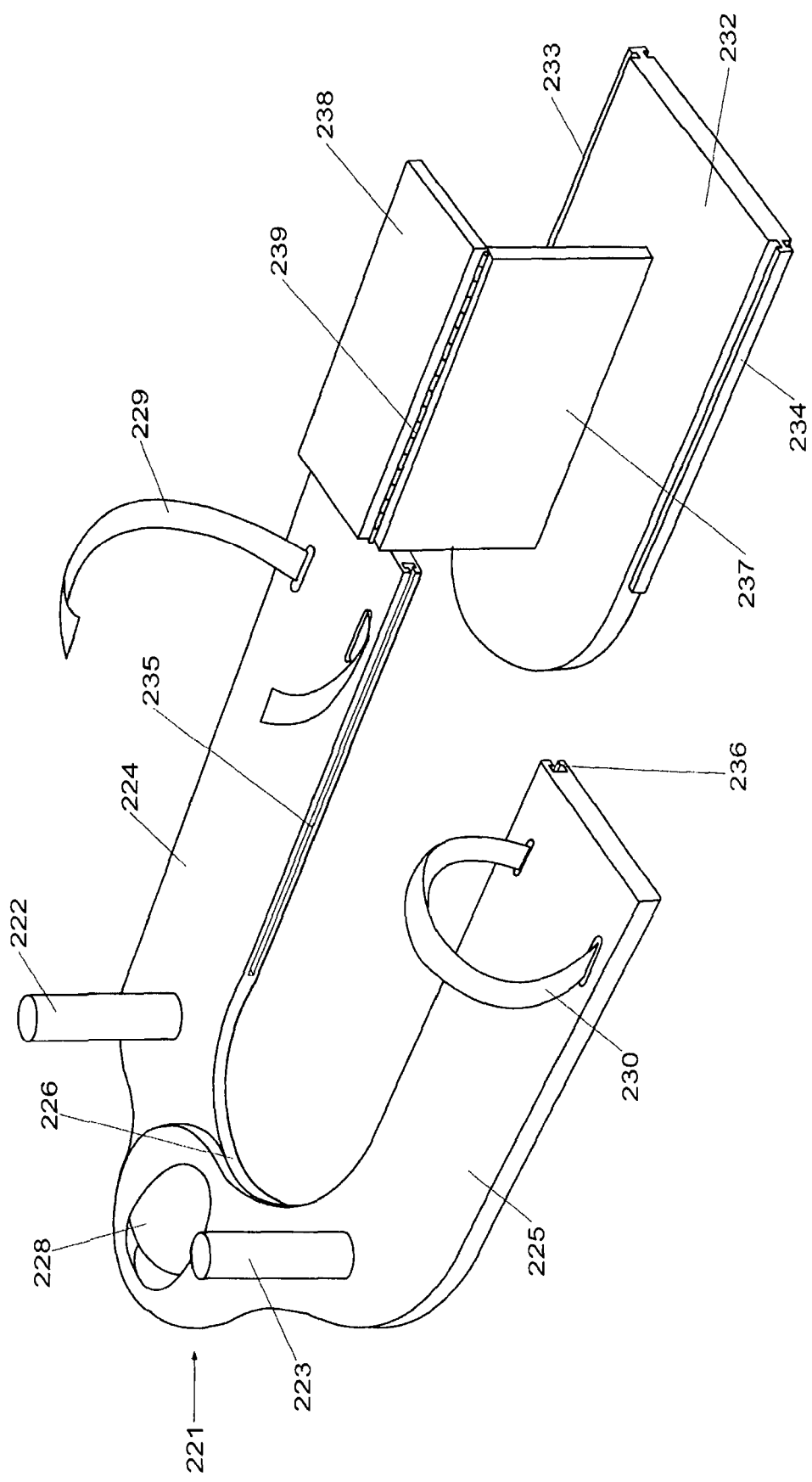
FIG. 18 is a perspective view of an articulated therapy aid according to the invention.

The therapy aid of FIG. 18 comprises a moveable structure 221 having two limbs 224 and 225 joined at pivot 226. Each limb 224 and 225 carries a handle 222 and 223 respectively. Each limb 224 and 225 has a strap 229 and 230 respectively capable of being secured to that limb. A computer mouse 228 is mounted on the structure 221 above pivot 226 to act as movement detector.

Figure 19:
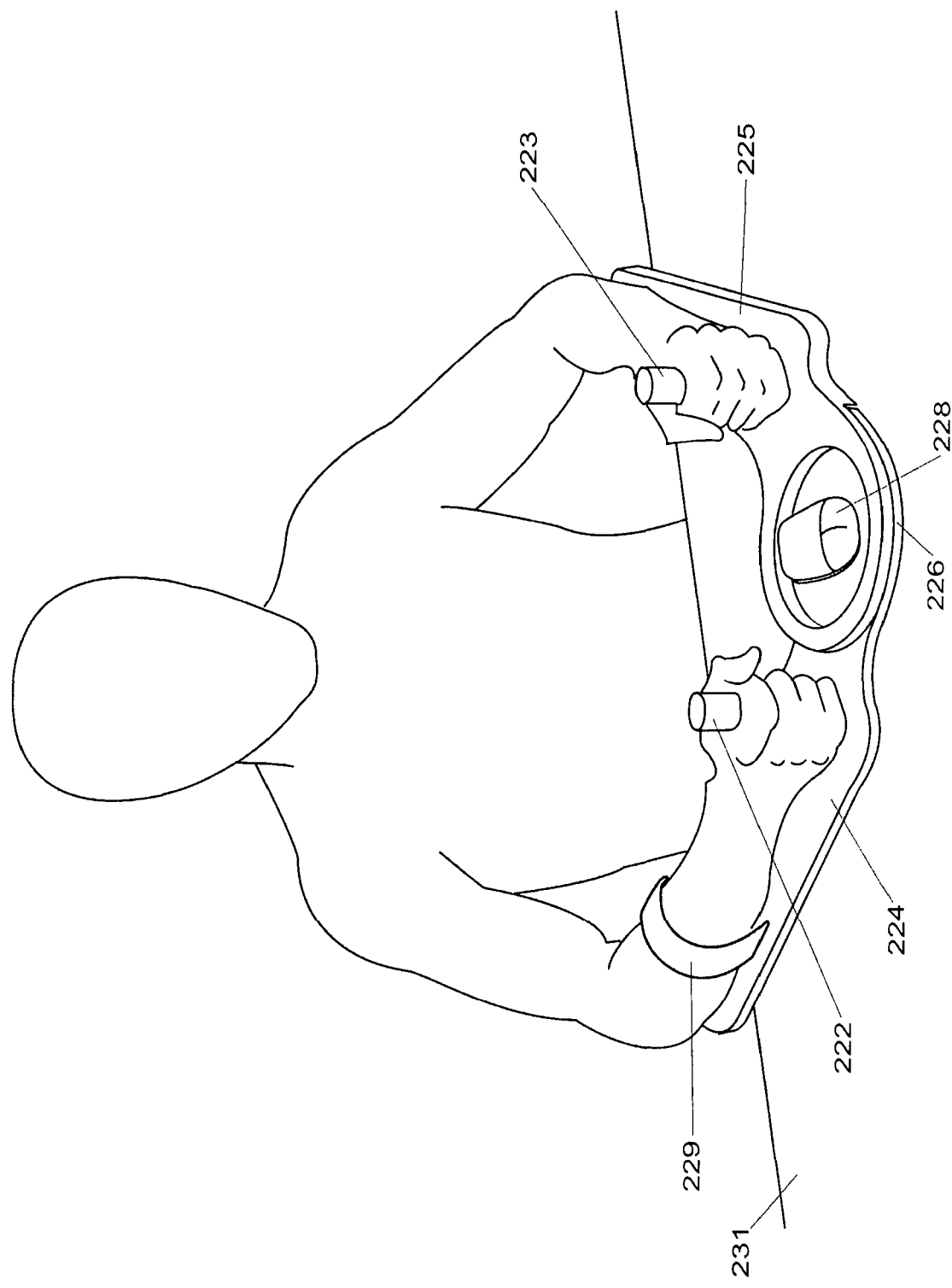
FIG. 19 is a perspective view showing the therapy aid of FIG. 18 in solo use by a patient.

In FIG. 19 the patient is shown moving the structure 221 across a surface 231. As the structure is moved, the limbs 224 and 225 can move towards each other or away from each other about the pivot 226. As the structure is moved towards the patient, the angle between the limbs 224 and 225 tends to increase. As the structure is moved away from the patient, the angle between the limbs 224 and 225 tends to decrease.

The therapy aid of FIG. 18 can be used with or without the auxiliary base board 232 shown in FIG. 18. Each lateral edge of base board 232 is formed with a tongue 233, 234. The limbs 224 and 225 of structure 221 each have a groove 235, 236 designed to accommodate tongues 233 and 234 respectively. The auxiliary base board 232 can carry a partition 237 and a cover 238, hinged at 239, for concealing a therapist's hand and arm.

Figure 20:
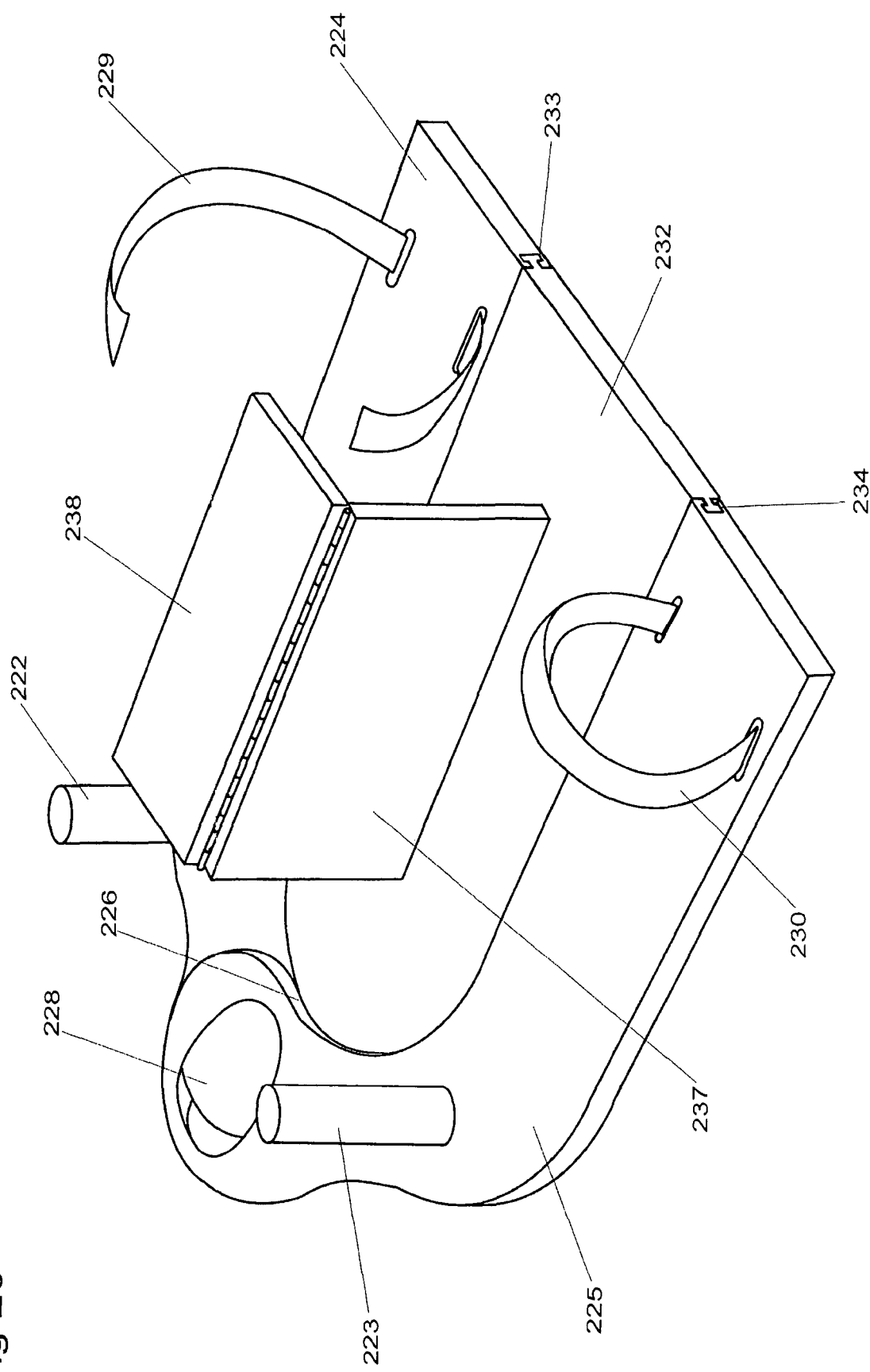
FIG. 20 is a perspective view showing the therapy aid of FIG. 19 fastened to form a rigid therapy aid.

The auxiliary base board 232 can be moved towards pivot 226 to engage the tongues 233, 234 with the grooves 235 and 236, thus fastening the limbs 224 and 225 together to form a rigid structure. Preferably the auxiliary board is moved far enough that the rear edge of auxiliary board 232 is flush with the rear edges of limbs 224 and 225 as shown in FIG. 20. The rigid structure thus formed can be used by a patient and therapist in the same manner as shown in FIG. 4.

The invention claimed is:

1. A rehabilitation therapy aid configured to facilitate rehabilitation of an arm of a patient comprising:
    a moveable structure configured to slide in any direction across a surface, the structure including:
        a base having a plate extending orthogonally from the base thereby defining a first side of the base and a second side of the base;
        a first support disposed on the base, the first support, the plate, and the base defining a first receptacle, the first receptacle configured to receive the arm of a patient, whereby the moveable structure is configured to be moved by the arm of the patient requiring therapy;
        a second support disposed on the base opposite the first support, the second support, the plate, and the base defining a second receptacle opposite the first receptacle, the second receptacle configured to receive an arm of a therapist or another arm of the patient, whereby the moveable structure is configured to be moved in the same direction by the arm of the therapist or by the another arm of the patient; and
    a sensor arranged so that the movement of the moveable structure relative to the surface is configured to be tracked, wherein the sensor includes an electro-optical system, the electro-optical system disposed in an aperture defined by the base and is configured to communicate with a computing device.

2. The rehabilitation therapy aid according to claim 1, further comprising a support board across which the moveable structure is disposed, the moveable structure configured to slide in any direction across a surface of the support board.

3. The rehabilitation therapy aid according to claim 2, wherein the sensor comprises a target pattern visible on the support board.

4. The rehabilitation therapy aid according to claim 1, wherein said first support further includes a first handle.

5. The rehabilitation therapy aid according to claim 4, for solo use by the patient, wherein the second support includes a second handle smaller than the first handle of the first support.

6. The rehabilitation therapy aid according to claim 1, wherein the sensor detects two-dimensional motion relative to the surface and is capable of recording the two-dimensional motion in digital form and transmitting it to the computing device.

7. The rehabilitation therapy aid according to claim 6, further comprising a monitor screen programmed to display the movements of the moveable structure tracked by the sensor.

8. The rehabilitation therapy aid according to claim 1, further comprising a strap coupled to the base and configured to secure the arm of the patient.

9. The rehabilitation therapy aid according to claim 1, wherein the base includes at least one of:
    a first plurality of apertures on the first side of the base configured to selectively receive the first support; or
    a second plurality of apertures on the second side of the base configured to selectively receive the second support.

10. The rehabilitation therapy aid according to claim 1, further comprising a cover pivotably coupled to the plate.

11. The rehabilitation therapy aid according to claim 10, wherein the cover is configured to conceal the arm of the therapist when the patient is moving the first support.

12. The rehabilitation therapy aid according to claim 1, wherein the electro-optical system is configured to enable the patient to control a cursor displayed by a monitor of the computing device.

13. The rehabilitation therapy aid according to claim 1, wherein the plate is configured to conceal the first support or the second support when viewed by the patient from a top perspective of the moveable structure.

14. A rehabilitation therapy aid configured to improve coordination of an arm of a patient comprising:
   a movable structure having: a base;
      a first support disposed on the base configured to enable the arm of the patient to engage the moveable structure, whereby the moveable structure is configured to be moved by the patient;
      a second support disposed on the base whereby the moveable structure is further configured to be moved in the same direction by a therapist;
      a cover configured to conceal the second support from a top perspective view of the patient; and
   a sensor arranged so that the movement of the moveable structure is configured to be tracked wherein the sensor includes an electro-optical system, the electro-optical system disposed in an aperture defined by the base and is configured to communicate with a computing device.

15. The rehabilitation therapy aid according to claim 14, wherein the sensor detects two-dimensional motion relative to a surface and is capable of recording the resulting information in digital form and transmitting it to the computing device.

16. The rehabilitation therapy aid according to claim 15, further comprising a monitor screen programmed to display the movements of the moveable structure tracked by the sensor.

17. The rehabilitation therapy aid according to claim 14, further comprising a support board whereby the moveable structure is disposed on the support board and configured to slide across the support board along any path.

18. The rehabilitation therapy aid according to claim 17, wherein the sensor comprises a target pattern visible on the support board;
   whereby the rehabilitation therapy aid enables the patient to see the movement of the moveable structure via the sensor.

19. A rehabilitation therapy aid configured to facilitate rehabilitation of an arm of a patient comprising:
   a moveable structure configured to slide in any direction across a surface, the structure including:
      a base having a first support and a second support;
      a first receptacle defined by the base and the first support, the first receptacle configured to receive a forearm of a patient;
      a second receptacle opposite the first receptacle, the second receptacle defined by the base and the second support, the second receptacle configured to receive a forearm of a therapist or another forearm of the patient,
   whereby the moveable structure is configured to be moved by the forearm of the therapist or by the forearm or another forearm of the patient; and
   a sensor configured to detect movement of the structure and provide an input to a computing device, wherein the sensor includes an electro-optical system, the electro-optical system disposed in an aperture defined by the base and is configured to communicate with a computing device.

* * * * *